United States Patent
Felix et al.

(10) Patent No.: US 12,168,137 B1
(45) Date of Patent: Dec. 17, 2024

(54) DE-ENERGIZABLE DEFIBRILLATION ASSEMBLY

(71) Applicant: Bardy Technologies, Inc., Vashon, WA (US)

(72) Inventors: Jason Felix, Vashon Island, WA (US); Gust H. Bardy, Carnation, WA (US); Cameron M. D. Bardy, Sammamish, WA (US)

(73) Assignee: Bardy Technologies, Inc., Vashon, WA (US)

( * ) Notice: Subject to any disclaimer, the term of this patent is extended or adjusted under 35 U.S.C. 154(b) by 0 days.

(21) Appl. No.: 18/401,199

(22) Filed: Dec. 29, 2023

Related U.S. Application Data

(63) Continuation-in-part of application No. 18/486,992, filed on Oct. 13, 2023, which is a continuation-in-part of application No. 18/156,318, filed on Jan. 18, 2023, now Pat. No. 11,794,026.

(51) Int. Cl.
*A61N 1/39* (2006.01)

(52) U.S. Cl.
CPC .............................. *A61N 1/39046* (2017.08)

(58) Field of Classification Search
CPC ................................................. A61N 1/39046
See application file for complete search history.

(56) References Cited

U.S. PATENT DOCUMENTS

| | | | | |
|---|---|---|---|---|
| 4,808,152 A | * | 2/1989 | Sibalis | A61N 1/044 604/20 |
| 5,314,502 A | * | 5/1994 | McNichols | H03K 17/30 604/20 |
| 5,562,607 A | * | 10/1996 | Gyory | A61N 1/0436 604/20 |
| 5,957,956 A | * | 9/1999 | Kroll | A61N 1/375 607/5 |

(Continued)

OTHER PUBLICATIONS

A.Capucci et al. "Community-based automated external defibrillator only resuscitation for out-of-hospital cardiac arrest patients," American Heart Journal, vol. 172, 2016, pp. 192-200, https://doi.org/10.1016/j.ahj.2015.10.018.

(Continued)

*Primary Examiner* — Eric D. Bertram
(74) *Attorney, Agent, or Firm* — Leonid Kisselev

(57) ABSTRACT

A completely de-energizable defibrillator is provided, allowing the electrical components of the defibrillator to be electrically unbiased while the defibrillator is not in use. The de-energizing of the defibrillator can be accomplished by separating the battery from the rest of the defibrillator circuitry with an electromechanical component, such as a power switch like a magnetically-triggered reed switch or a mechanically-triggered switch. The de-energizing of the defibrillator can also be accomplished by including in the defibrillator a removable piece of insulating material between the battery and the circuitry. The de-energizing of the defibrillator can also be accomplished by a change in configuration or position of the moveable components of the (Continued)

AED. The preparation of the defibrillator for use triggers the circuitry to become energized. Additionally, the microcontroller unit of the AED includes features to prevent computational errors due to cosmic radiation, including lockstep processors and error detection code.

10 Claims, 23 Drawing Sheets

(56) References Cited

U.S. PATENT DOCUMENTS

| | | | | |
|---|---|---|---|---|
| 6,377,848 | B1* | 4/2002 | Garde | A61N 1/30 |
| | | | | 604/20 |
| 6,662,056 | B2* | 12/2003 | Picardo | A61N 1/0472 |
| | | | | 607/142 |
| 7,072,712 | B2 | 7/2006 | Kroll et al. | |
| 7,495,413 | B2* | 2/2009 | Vaisnys | A61N 1/3975 |
| | | | | 320/103 |
| 9,168,386 | B2* | 10/2015 | Schwibner | G06F 21/31 |
| 9,889,311 | B2 | 2/2018 | Horseman | |
| 10,093,675 | B2 | 10/2018 | Zahajska et al. | |
| 10,449,380 | B2 | 10/2019 | Andrews et al. | |
| 10,543,376 | B2 | 1/2020 | Beyer et al. | |
| 10,668,296 | B2 | 6/2020 | Meir | |
| 10,773,091 | B2 | 9/2020 | Andrews et al. | |
| 10,799,709 | B2 | 10/2020 | Teber | |
| 11,077,311 | B2 | 8/2021 | Beyer et al. | |
| 11,097,121 | B2 | 8/2021 | Beyer et al. | |
| 11,213,454 | B1 | 1/2022 | Shaker et al. | |
| 11,305,128 | B1 | 4/2022 | Beyer et al. | |
| 11,318,322 | B2 | 5/2022 | Beyer et al. | |
| 11,547,863 | B1* | 1/2023 | Shaker | A61N 1/3904 |
| 2003/0080712 | A1* | 5/2003 | Tamura | A61N 1/3975 |
| | | | | 320/103 |
| 2004/0044371 | A1 | 3/2004 | Tamura et al. | |
| 2004/0143297 | A1* | 7/2004 | Ramsey, III | A61N 1/3975 |
| | | | | 607/5 |
| 2005/0021094 | A1* | 1/2005 | Ostroff | A61N 1/3906 |
| | | | | 607/5 |
| 2006/0178865 | A1* | 8/2006 | Edwards | A61N 1/3993 |
| | | | | 704/1 |
| 2009/0256527 | A1* | 10/2009 | Welsch | A61M 5/172 |
| | | | | 320/136 |
| 2011/0202101 | A1* | 8/2011 | Tan | G09B 19/003 |
| | | | | 607/7 |
| 2014/0317914 | A1 | 10/2014 | Shaker et al. | |
| 2014/0324111 | A1* | 10/2014 | Wu | A61N 1/3968 |
| | | | | 607/7 |
| 2016/0250492 | A1* | 9/2016 | King | A61N 1/3987 |
| | | | | 607/7 |
| 2017/0157415 | A1 | 6/2017 | Horseman | |
| 2018/0140859 | A1 | 5/2018 | Meir | |
| 2018/0280708 | A1* | 10/2018 | Escalona | H02J 50/10 |
| 2018/0318592 | A1 | 11/2018 | Smith | |
| 2019/0044362 | A1* | 2/2019 | Beyer | H02J 7/00714 |
| 2019/0117989 | A1* | 4/2019 | Andrews | H02J 7/00 |
| 2019/0356492 | A1* | 11/2019 | Picco | H04L 67/125 |
| 2020/0038649 | A1* | 2/2020 | Manicka | A61M 5/14276 |
| 2021/0093877 | A1* | 4/2021 | Beyer | H02J 7/007182 |
| 2023/0041857 | A1* | 2/2023 | Prutchi | A61N 1/378 |
| 2023/0089192 | A1* | 3/2023 | Bennett | A61N 1/046 |
| | | | | 607/142 |

OTHER PUBLICATIONS

J. W. Gundry et al. "Comparison of Naive Sixth-Grade Children With Trained Professionals in the Use of an Automated External Defibrillator," Circulation Oct. 19, 1999; Downloaded from http://ahajournals.org by on Oct. 22, 2022.

D. Aschieri et al. "Ventricular Fibrillation Recurrences in Successfully Shocked Out-of-Hospital Cardiac Arrests," Medicina 2021, 57, 358. https://doi.org/10.3390/medicina57040358.

G. H. Bardy et al. "A Prospective Randomized Evaluation of Biphasic Versus Monophasic Waveform Pulses on Defibrillation Efficacy in Humans," Cardiac Pacing, Biphasic Versus Monophasic Defibrillation, JACC vol. 14, No. Sep. 3, 1989:728-733.

G. H. Bardy et al. "A Prospective Randomized Comparison in Humans of Biphasic Waveform 60-μF and 120-μF Capacitance Pulses Using A Unipolar Defibrillation System," Originally published Jan. 1, 1995 https://doi.org/10.1161/01.CIR.91.1.91 Circulation. 1995;91:91-95.

HeartSine® samaritan® PAD 350P/360P AEDs Semi-automatic/fully automatic public access defibrillators, "Compact, easy-to-use, lifesaving technology for public access" H009-032-340-AE_350P_360P_Data_ENUS_0521_web-3.

HeartSine® samaritan® PAD 350P/360P Connected AEDs Semi-automatic/fully automatic public access defibrillators with integrated Wi-Fi® connectivity; "Readiness matters," H009-043-010-AD_Connected_350P_360P_Data_ENUS_0521_web.

"Defibtech Lifeline ECG Semi-Automatic Defibrillator with ECG Display Technical Specifications+," DAC-A2702EN-BC Issued: Jan. 15, 2021. Defibtech, LLC • Guilford, CT 06437 USA • 1-203-453-4507 • 1-866-DEFIB-4U (1-866-333-4248) www.defibtech.com.

https://web.archive.org/web/20231221183725/https://en.wikipedia.org/wiki/Reed_switch, cached on Dec. 21, 2023.

https://www.digikey.com/en/product-highlight/k/keystone/battery-insulating-pull-tabs, cached on Feb. 18, 2019.

* cited by examiner

100

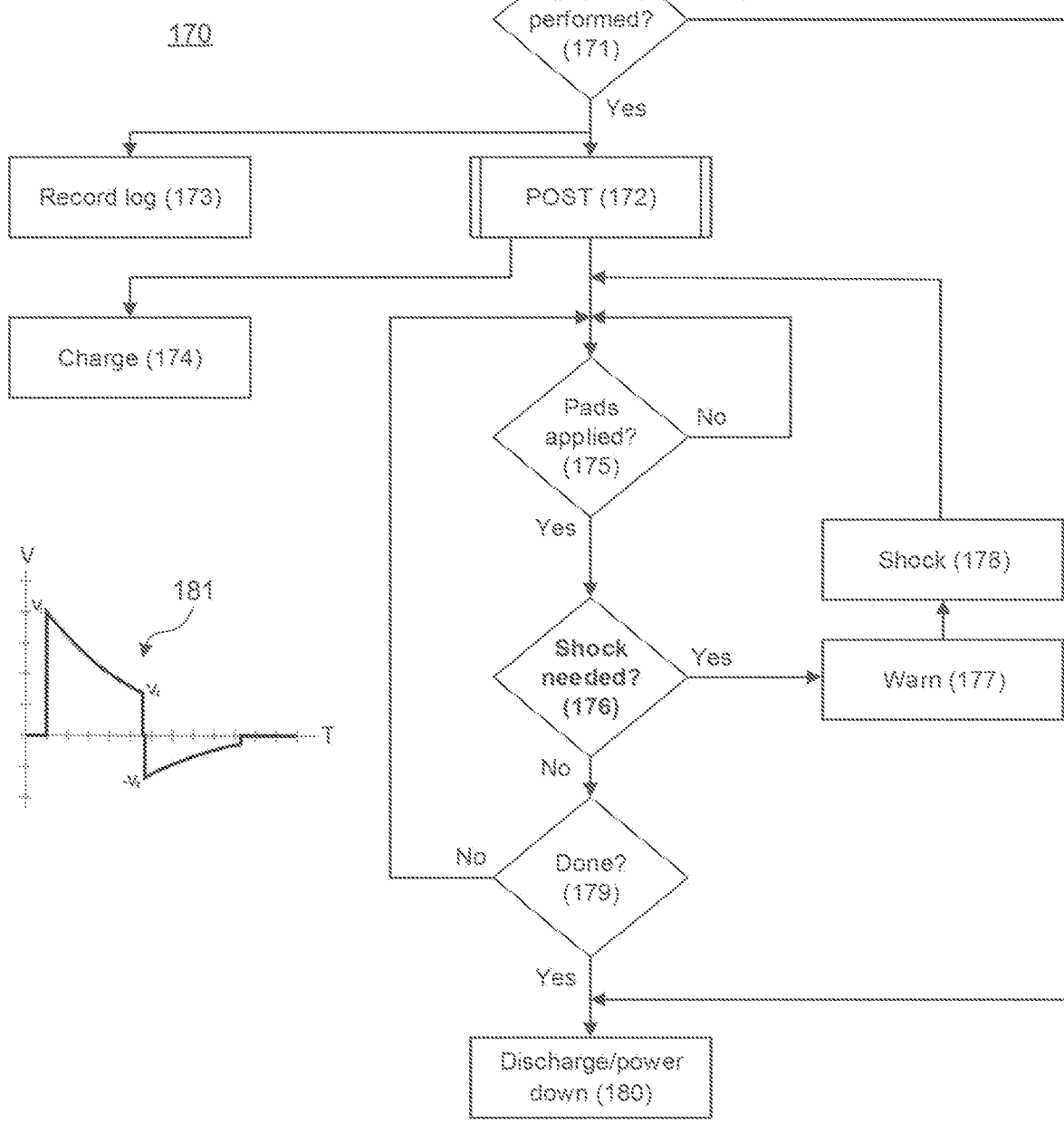

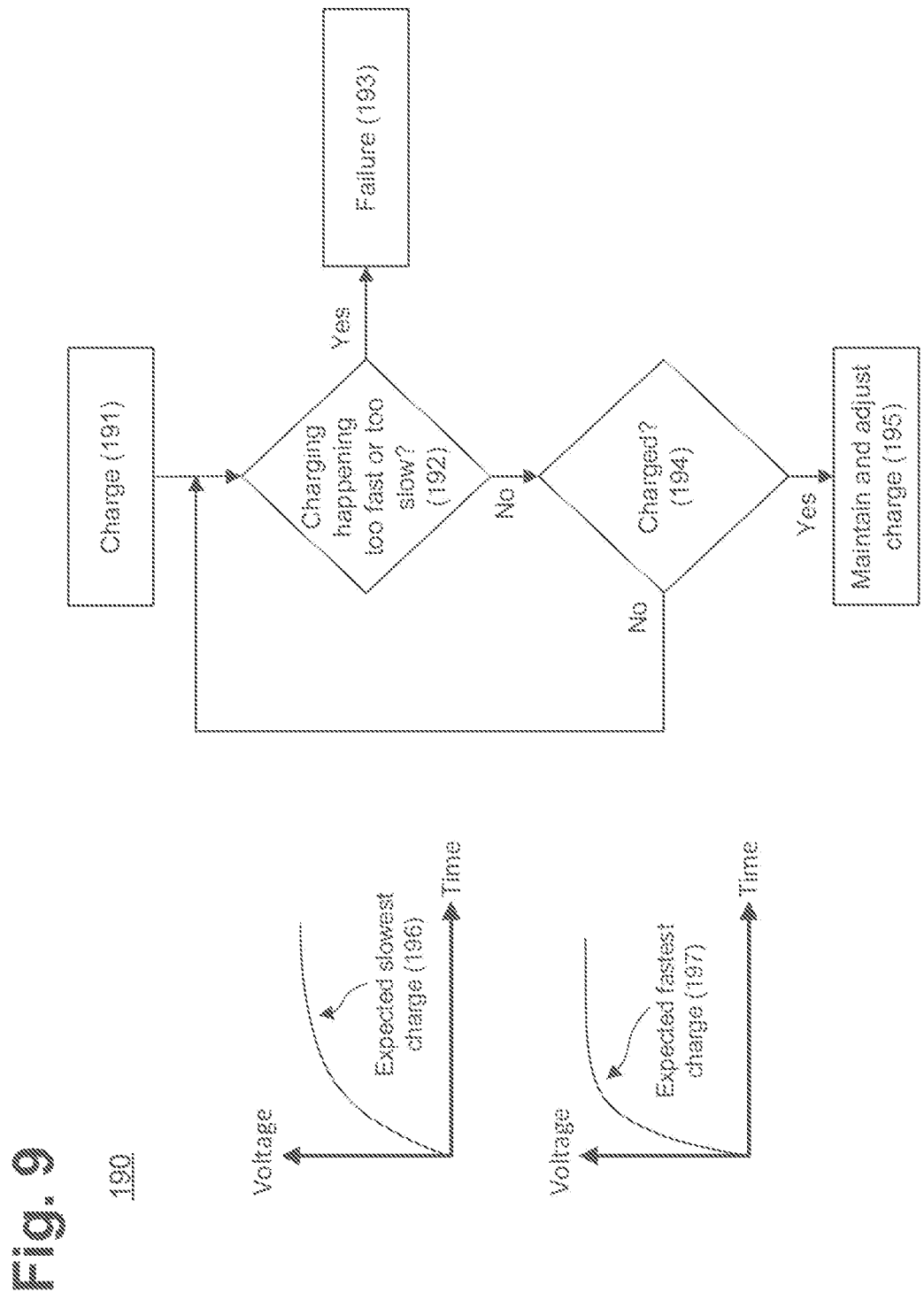

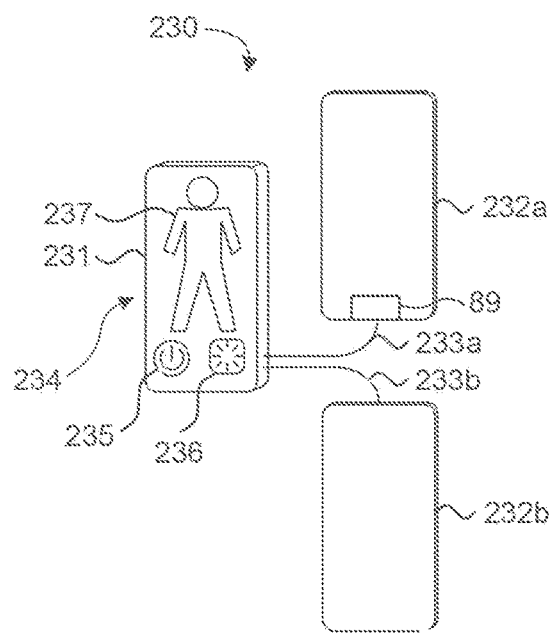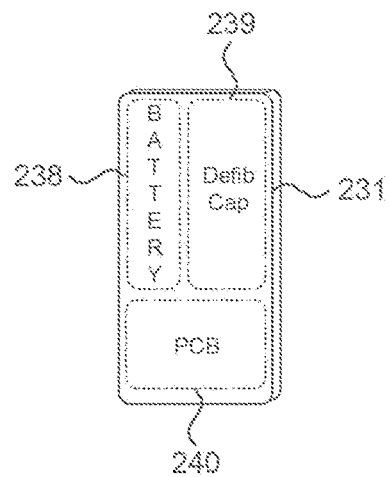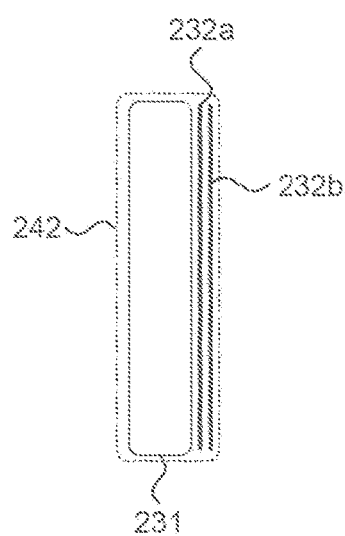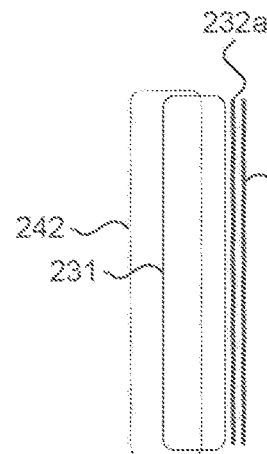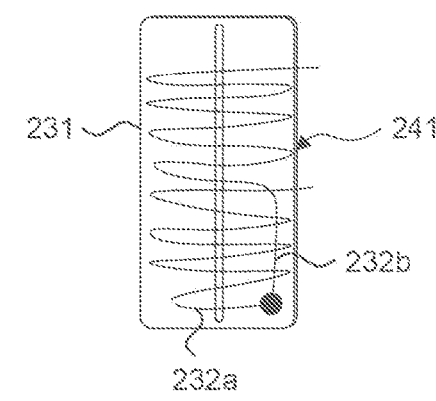

340

360

71

410

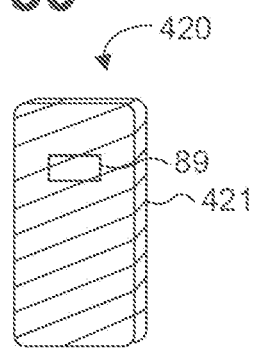

DE-ENERGIZABLE DEFIBRILLATION ASSEMBLY

FIELD

This invention relates in general, to circuits for generating defibrillation waveforms and in particular, to a defibrillator that can be stored and maintain readiness long-term in a de-energized state.

BACKGROUND

Sudden cardiac arrest (SCA) is a significant cause of mortality throughout the world and remains a major public health concern causing about 300,000 to 450,000 deaths each year in the United States alone, despite the broad scale teaching of cardiopulmonary resuscitation (CPR) and the implementation of public access automated external defibrillators (AED) in hospitals, ambulances, and other public locations, like airports and stadiums. More than 9 of 10 SCA victims of SCA die, even in locales with advanced medic response systems. In most locations globally, the death rate approaches 100%.

SCA occurs when the heart suddenly and unexpectedly stops pumping blood, most commonly caused by a chaotic cardiac rhythm disorder known as ventricular fibrillation (VF). VF is a lethal heart rhythm abnormality that causes the ventricles of the heart to quiver, resulting in ineffective contraction of the ventricles and a failure to pump blood. Accordingly, blood pressure plummets and blood delivery to the brain and all bodily organs essential ceases and yielding loss of consciousness in 5-10 seconds.

SCA from VF constitutes the most time-critical emergency in medicine and is universally lethal within 10-20 minutes without prompt medical attention, specifically the delivery of a high-voltage, high-energy shock across the chest via a defibrillator, the only method known to stop VF. Preferably such a shock is delivered within 5 minutes of the onset of VF upon rapid deployment of easily accessible defibrillation pads.

Because victims of VF collapse within 5-10 seconds, lose consciousness, and become unresponsive, only someone that is physically near the victim has a meaningful chance at preventing death. The chance of survival rapidly decreases 7-10% per minute from onset of VF and, after 10 minutes, resuscitation rarely succeeds, even with CPR, and even if an AED is used, as the heart and brain will have suffered irreversible injuries. Consequently, ensuring that people have immediate access to an AED is both absolutely essential to saving lives from cardiac arrest, where every minute counts, and critically dependent upon a design that allows personal pocketability, such that the AED is compact enough to be carried everywhere with an individual, including in a pocket.

AEDs made publicly available, however, have not meaningfully addressed the problem of SCA in part because they are not designed to be easily wearable, like a cell phone that is carried by nearly every individual today. By various accounts, there are approximately 3.2 to 4.5 million AEDs currently deployed in public places in the United States, yet an estimated more than 30 million AEDs are needed to provide sufficient coverage to meaningfully improve cardiac arrest survival rate nationally. Moreover, despite this disparity between the number of devices versus the estimated need, increasing the number of public access AEDs by an order of magnitude would be neither practical in terms of cost or execution nor would such an increase truly address the problem that SCAs primarily occur in places other than where public access AEDs are found and, even so, rarely are readily available, given their bulk, even if such devices were present in the home. More than 80-90% of VF cases occur in or near the home or during routine activities of daily living, like yard-work and gardening, driving, personal recreation, and so on. These represent locations where public access AEDs are not usually found. Moreover, public access AEDs are rarely deployed or used in such locations where SCAs typically happen and, if they are, their use often comes far too late. Thus, the problem of resuscitating victims from VF is inexorably linked to time and proximity to an AED, which are, in turn, inexorably linked to convenience of use, which, in turn, is a direct consequence of AED cost, size and weight. Accordingly, to make a positive impact on survivability of SCA requires a different approach to AED deployment. One solution would be to provide an AED that is first and foremost pocket-sized and modest in weight and cost, so that AEDs become practically ubiquitous, similar to a mobile phone.

The high cost and bulk of conventional public access AEDs are mainly due to the design choices of reusability, integrated telemetry and functionality intended to constantly perform and disclose the results of multi-use readiness checks. Typical AEDs perform self-testing constantly, depleting their battery, and causing wear on critical components. These design choices require large and complex circuits and components that will survive constant testing and the stress induced therein. Several AED product recalls have shown this practice to prematurely degrade components, resulting in an AED becoming non-functional when needed. AEDs are typically designed to eliminate failure modes, which, paradoxically, results in large and complex systems that are expensive and prone to failure. For example, conventional public access AED capacitors are often rated for operation at 90° C. and 20,000 back-to-back pulse discharges, conditions that do not remotely resemble the typical use case under any conceivable scenario which is 1-3 shocks in normal environmental conditions. Moreover, reusability requirements mean that the batteries must be able to store enough energy to defibrillate multiple patients, perform simulated use testing, as well as have circuits that are able to sense when the device will not be "rescue ready" in the future.

The above list of historical technical design features, that have not meaningfully improved survival of SCA over the past 30 years are key factors that effectively restrict deployment of public access AEDs to healthcare providers, first responders, and public areas that are legally required to have an AED, all of which make existing AEDs relatively unavailable and of no use for the majority of VF emergencies that occur at or near the home away from public access AEDs. Moreover, public access AEDs are packaged in large carrying cases weighing several pounds that are too bulky to be convenient for ubiquitous use by the public. Despite their design intent of simplicity for use, rescuers are often in a state of confusion, even panic. Today's AEDs are geared toward the SCA-informed user, rather than the stressed, often terrified rescuer. As a consequence, an intuitive, ultra-simple deployment strategy is critical. Finally, AEDs typically cost between $1000 to $2200, which is too expensive for the average person to buy or to serve as a personal safety tool to accompany activities of daily living.

Further, the shelf life of typical AEDs is limited by the high rate of degradation of both hardware components and firmware code of such AEDs. Such defibrillators are always energized, with power constantly provided to a majority of the control components of the defibrillator. Such defibrillators spend the majority of their time in a low-power state and enter a high-power state periodically to test themselves. Multiple recalls of such defibrillators show that an always-on approach results in a high rate of wear, causing the defibrillators to suffer component breakdown and failure. In particular, being always powered on makes typical defibrillators vulnerable to formation of intermetallics between circuit elements, especially in integrated circuits, which negatively impact reliability of the circuit elements. Further, the defibrillation control circuitry, when powered on, is particularly susceptible to cosmic ray strikes, which among other damage, can cause computational errors by changing the code of the firmware controlling the defibrillator, as well as active memory contents by inducing unexpected bit transitions. Such computational errors can have life-threatening consequences, and thus a defibrillator with such errors may no longer be safe to use.

Therefore, a need remains for providing a reliable, lightweight, pocket-sized AED simply designed for single use by naïve and frightened rescuers. Preferably, the AED, including housing, is both secure, durable, yet immediately deployable by a rescuer in the most dire of life and death circumstances.

SUMMARY

A compact, pocket sized, lightweight AED promotes widespread use and helps ensure availability when needed. The electrical components of the AED, as well as the housing or case of the AED, should be sized to fit within a pocket for ease of carrying for continuous availability. Further, the case should accommodate the medically necessary electrical components of a defibrillator, like a relatively large high-voltage capacitor, while simultaneously allowing rapid defibrillation, shock pad release, and use by an average citizen within a short time, such as within one minute of victim collapse, without need for contemplation or further deployment complexities other than application of the shock pads to the right infraclavicular and left inferolateral anterior thorax beneath the heart. Facilitation of effective use requires that purposeful movement of one or more components of the carrying case triggers charging of the AED for intended ventricular fibrillation detection and shocks promptly upon application, while also guarding against unintended opening of the case.

The AED components that facilitate a pocket size (i.e., a cell phone size) AED must not only have an innovative shock pad housing capable of minimalist dimensions, but house the electronics, while also being capable of immediate and intuitive pad deployment and effectively shocking the victim within one minute by a distressed and excited average citizen rescuer. Such a rapidly deployable pocket size defibrillator case must include a circuit enclosure having a bottom surface surrounded by four walls forming a cavity to house an energy storage circuit adapting to electronic component variability, including relatively large components like the capacitor. An electrode enclosure includes a bottom surface surrounded by four walls forming a cavity to house electrode pads and is stacked on top of the circuit enclosure. A cover includes a substantially flat surface positioned over the electrode enclosure and moveable to allow access only to the electrode enclosure. Such an enclosure harbors routes of circuit connection and rescuer activation. Further, the AED is de-energizable, allowing the electrical, memory and computational components of the AED to be electrically unbiased while the AED is not in use. This strategy mitigates the formation of intermetallics in the AED's internal circuitry, especially integrated circuits and decreasing the degree of wear. Furthermore, the lack of biasing of high-voltage components decreases wear from the formation of conductive anodic filaments in the circuit board substrate. The de-energizing of the AED can be accomplished by physically and electrically isolating the energy storage element such as a battery, ultracapacitor or hybrid battery from the rest of the AED circuitry with an electromechanical component. This could be a power switch such as a button, a magnetically-triggered reed switch or a mechanically-triggered interlock. The de-energizing of the AED can also be accomplished by including in the AED a removable piece of insulating material at some point in the pathway between the battery and the electrical components. The preparation of the AED for use, or the use of the AED, causes the circuitry to become energized. Additionally, the microcontroller unit of the AED can include features to prevent computational errors due to cosmic radiation from negatively affecting AED performance, including lockstep processors, error detection code, and other functional safety mechanisms which provide additional layers of reliability. Moreover, a de-energized defibrillator increases battery life, thus allowing a reduction in battery size due to lower capacity need. The reduction in size of batteries is important for AED accessibility leading to better patient outcomes.

In one embodiment, a de-energizable defibrillation assembly is provided. The assembly includes an electromechanical component; an energy storage element that supplies power to the electromechanical component; and circuitry configured to generate a defibrillation waveform, wherein the circuitry is isolated from the energy storage element by the electromechanical component.

In a further embodiment, a defibrillation assembly with an isolatable power source is provided. The assembly includes an energy storage element; circuitry configured to generate a defibrillation waveform; and an insulating wedge positioned to isolate the circuitry from the energy storage element, wherein the energy storage element provides power to the circuitry upon a removal of the insulating wedge from the position.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 8 is a flow chart showing a method for operating a disposable single use pocketable AED in accordance with one embodiment.

FIG. 9 is a flow chart showing a charging routine with out-of-bounds failure detection for use in the method of FIG. 8 in accordance with one embodiment.

FIG. 10 is a front view showing a disposable single use pocketable AED with dual free-floating electrodes in accordance with one embodiment.

FIG. 11 is a cut-away view showing block component groups contained within the disposable single use pocketable AED of FIG. 10.

FIG. 12 is a side view showing the disposable single use pocketable AED of FIG. 10 with the housing and dual free-floating electrodes stowed in a carrying case.

FIG. 13 is a side view showing the disposable single use pocketable AED of FIG. 10 with the housing and dual free-floating electrodes partially deployed from the carrying case.

FIG. 14 is a back view showing the cable management system of the disposable single use pocketable AED of FIG. 10.

FIG. 30 is a diagram showing an AED covered with packaging in which a trigger for activating the AED is embedded in accordance with one embodiment.

DETAILED DESCRIPTION

Figure 1:
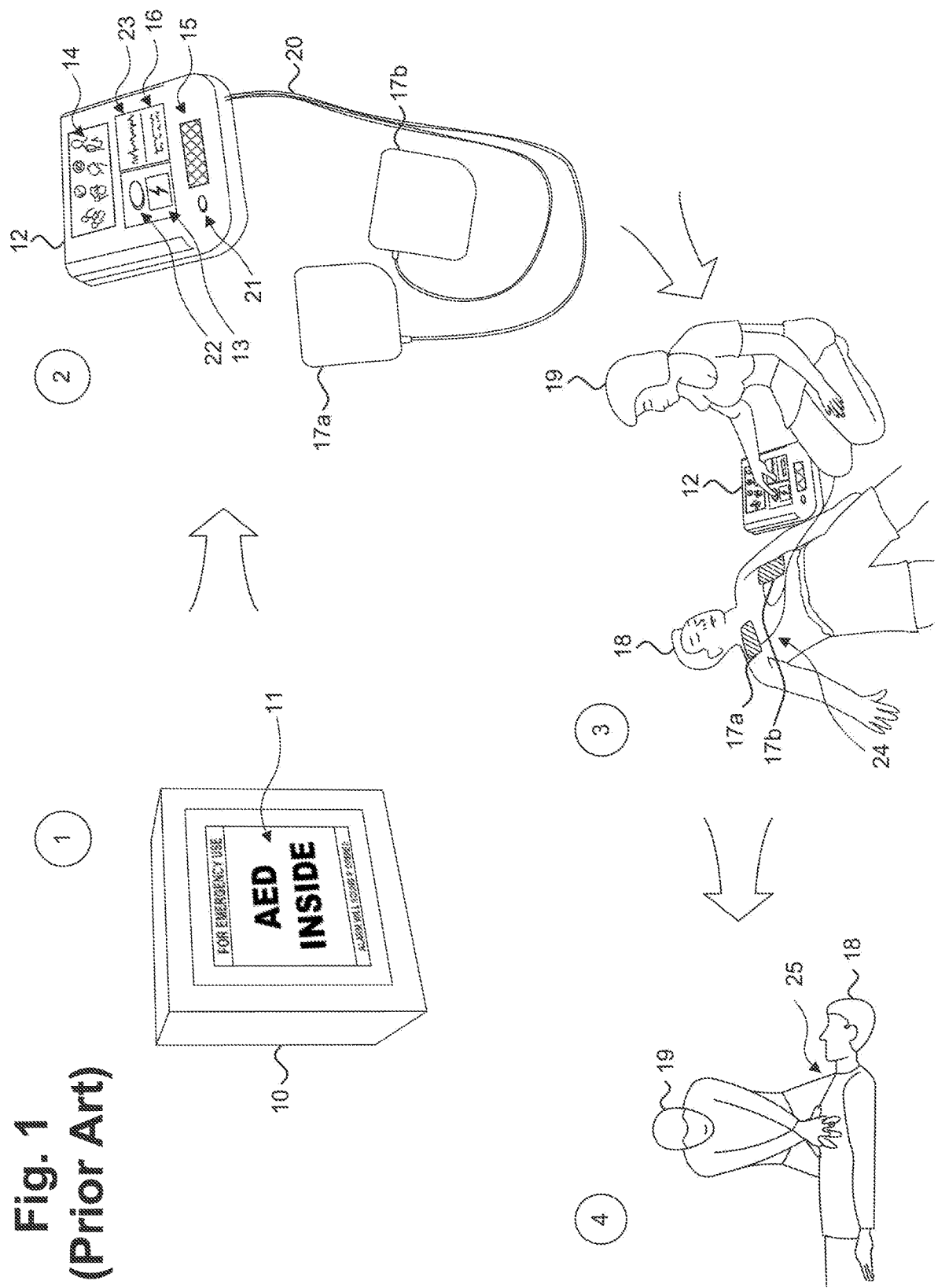
FIG. 1 is a process flow diagram showing, by way of example, a typical prior art use of a public access AED in an SCA situation.

There has been a push to deploy public access AEDs in busy often-frequented places, such as airports, restaurants, casinos, shopping centers, and stadiums. Public access AEDs urge delivery of defibrillation shocks by a bystander in an attempt to restore normal cardiac rhythm. Such use only addresses a modest proportion of SCA victims and are typically deployed by unemotionally involved witnesses, often professional medical personnel that happen upon the victim. FIG. 1 is a process flow diagram showing, by way of example, a typical prior art use of a public access AED 12 in an SCA situation. Public access AEDs are designed for repeated use and harbor a complex array of visual, auditory, and manual button-oriented instructions. They require, at minimum, monthly checks and relatively frequent pad and battery replacements. Despite their distribution, there has been little change in the death rates from SCA because most SCA occurs in the home or in average activities of daily living with their accessibility being limited.

In a typical example of a public AED use, a victim 18 has suffered suspected cardiac arrest while in the company of a public rescuer 19. The terms "victim" and "patient" are used interchangeably and refer to the individual that is receiving emergency care for a possible cardiac arrest. Similarly, the terms "rescuer," "bystander" and "user" are used interchangeably and refer to the individual who is actively providing the emergency care whether or not he knows the victim through the use of a public access AED.

When SCA is suspected, often when a victim suddenly loses consciousness and collapses, a rescuer 19 must take immediate action to assist the victim 18. After ideally first calling 9-1-1, the rescuer 19 should check the victim 18 for a pulse and, if absent, begin basic life support maneuvers (BLS), which begins by first locating and obtaining a public use AED 12 (step (1)). Note that there are two main categories of AEDs, either of which may be found in use as a public use AED. Some AEDs automatically deliver shocks without rescuer action when pads are applied, following VF detection. Most AEDs, however, are semi-automatic and require the rescuer to manually trigger a shock with a button or device control. The portable AEDs carried by emergency medical services (EMS) personnel are generally designed as semi-automatic AEDs that include physiological monitoring tools for both basic and advanced life support, as well as include advanced CPR feedback and vital signs patient monitoring.

A typical public access AED 12 is located where the general public ordinarily has access and is mounted in some type of protective housing 10, such as a display case, wall cabinet or kiosk. Public access AEDs are designed for long-term reuse and to be available to save multiple victims over their service lifetime. Thus, these devices are physically robust to withstand rough and repeated use, if properly maintained during periodic checks. Such complicating factors that add to unit cost and size, include these maintenance obligations as well as telemetry functionality needed to prevent failures and sustain readiness over time. Further, the public access AED 12 itself is portable and therefore susceptible to being misplaced or stolen; the protective housing 10 helps to keep the public access AED 12 secure and available until needed. Theft can be common in major cities and yet the AED must remain readily available and therefore replaced if their loss is noted by authorities. Note that, despite being portable, a public access AED kit is bulky and weighs several pounds, which makes carrying a public access-type AED on an everyday basis impractical for nearly all individuals, even though wider AED availability and use could help save more lives. In addition, both the electrodes and batteries of public access AEDs have expiration dates and must be replaced upon their respective expiry every one to three years. Moreover, these traditionally designed AEDs must undergo periodic operational testing that may require that the defibrillation circuit be energized, resulting in a depleted battery charge as well as commonly and prematurely degrading the circuit, which paradoxically contradicts the original design intent of periodic testing.

Returning to the steps of AED use in public, once the rescuer 19 locates and obtains an AED, the rescuer must activate the AED 12, which generally entails pressing an "On" button or other simple-to-use control (step (2)). Conventional public use AEDs 12 are packaged in a large carrying case that contains the AED circuit, including sensing and defibrillation circuit and battery, a pair of shock paddles (not shown) or, more commonly, adhesive dermal electrode pads 17*a-b* connected by a set of leads 20, and support accessories (not shown), such as gloves and a face shield. Note that shock paddles and adhesive electrode pads are both acceptable modes for delivering defibrillation shocks and when used correctly, are equally efficacious. Conventional shock paddles and electrode pads are generally about 8-12 cm in length, rectangular, and intended to conform to the human thoracic anatomy.

As most rescuers will be lay bystanders, albeit often with medical background, public use AEDs generally provide visual and usually verbal instructions 14 on assessing the victim's breathing and placement of its electrode pads 17*a-b* on the victim's chest 24 (step (3)). The AED includes a set of necessary controls, typically an "On" button 21 and, if the AED is semi-automatic, a "Shock" button 22 to manually deliver a defibrillation shock by the rescuer, plus a warning indicator 13 that the AED is charged and ready to deliver a defibrillation shock. To activate the public use AED 12, the rescuer 19 presses the "On" button 21. The visual instructions 14 are typically supplemented with speaker-generated voice prompts 15, display-generated text prompts 16, in some cases, an electrocardiogram (ECG) 23, or some combination of voice prompts, text prompts and an ECG. The American Heart Association (AHA) and European Resuscitation Counsel (ERC) publishes guidelines outlining a recommended sequence of visual and voice prompts to help rescuers in proper use of AEDs. See, 2010 *American Heart Association Guidelines for CPR and ECC*; Supplement to *Circulation*, Vol. 192, Issue 18 (Nov. 12, 2010). *European Resuscitation Council Guidelines for Resuscitation* 2010, *Resuscitation* Volume 81 (October 2010). Despite such control over rescuer interactions with the classically designed AED, little progress has been made in SCA survival, perhaps due to the confusion and valuable time loss, such visual, auditory, communicative, and mechanical commands yield especially to naïve lay users. The time loss alone in attempting to follow complex instructions is sufficient to limit resuscitation success especially for the elderly or uninformed rescuer.

The electrode pads 17*a-b* must be applied by the rescuer 19 to be in direct contact with the victim's skin. With traditional AED kits, many include a razor to shave any hair off the victim's skin where the electrode pads 24 are to be placed. The intent is to maximize the transit of current through the heart. However, shaving the hair costs valuable time. This is routinely done despite the absence of data to show meaningful improvement in current flow through the thorax by shaving hair. The practice is a legacy of in-hospital experience whereupon pad removal from hairy chests during elective cardioversion are known to be painful. In the case of a cardiac arrest, however, such concerns are trivial compared to saving a life. Even a one-minute loss in shock delivery carries a 10% mortality rate. Later in the resuscitation efforts, such delays are lethal and partly contribute to the poor results in SCA resuscitation. Accordingly, our casing design in this application is informed by such prior time-wasting considerations as will be discussed shortly.

Public access AEDs are designed for use on multiple victims, which leads to a complex and typically over-engineered design that leads to high cost and long-term maintenance obligations and frequent failures, as well as complexity of use by the truly lay user.

The life-saving benefits of AEDs can be efficaciously provided to every person, everywhere, and on a 24/7/365 basis through a disposable, single-use AED that is small enough to be truly portable, for instance by fitting in an average-sized pocket. A single use AED, that is, a device that is available to therapeutically treat one instance of SCA, significantly streamlines and simplifies the design requirements of the AED and accordingly makes it possible to house the AED in a small pocketable form factor. Periodic maintenance is not required, as the disposable nature of the pocket AED implies the device will be discarded before needing to undergo maintenance or other testing prior to use on a patient. As well, the reliability level of the electronic components can be selected to be appropriate to accommodate a single use scenario, rather than repeated uses over an extended service life of many years, limiting complexity and improving durability, such as been shown in military applications. Similarly, the battery can be smaller and lighter, as battery life will not be depleted by long shelf life and telemetry transmissions related to diagnostic routines and maintenance cycles. Further, the use of such simplified electronic components and battery technologies lowers cost and allows disposability to be realized. Finally, to encourage being carried by users at all times, the pocket AED is sized comparably to a large smartphone, for instance, in the range of 2.25 to 3.625 inches wide, 5.25 to 7 inches tall, and 0.25 to 1.875 inches deep, and of similar weight, for example, in the range of 130 to 945 grams.

Figure 2A:
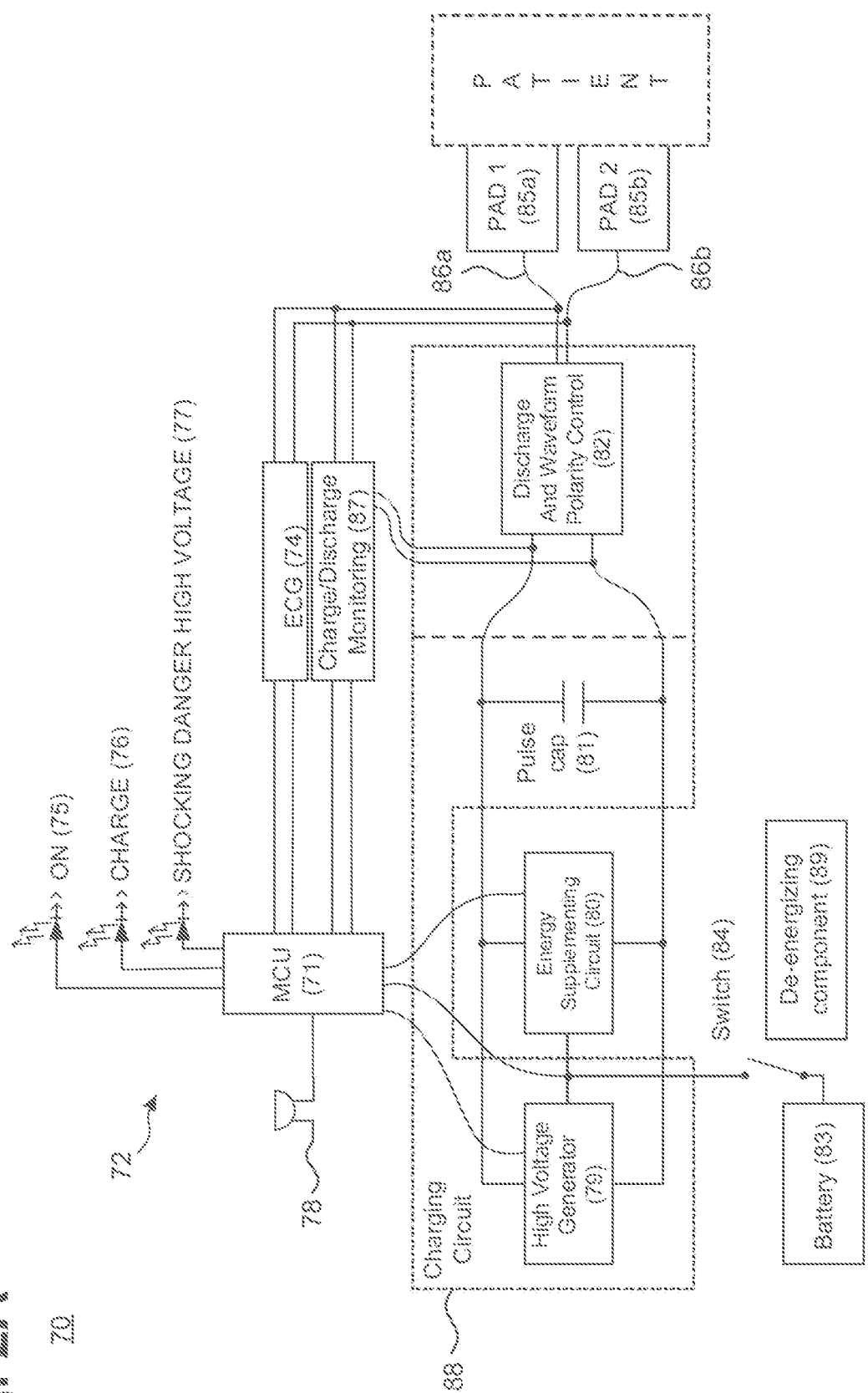
FIGS. 2A-2B are block diagrams showing functional components and a user interface for a de-energizable defibrillation assembly that includes a disposable single use pocketable AED in accordance with two embodiments.
Figure 2B:
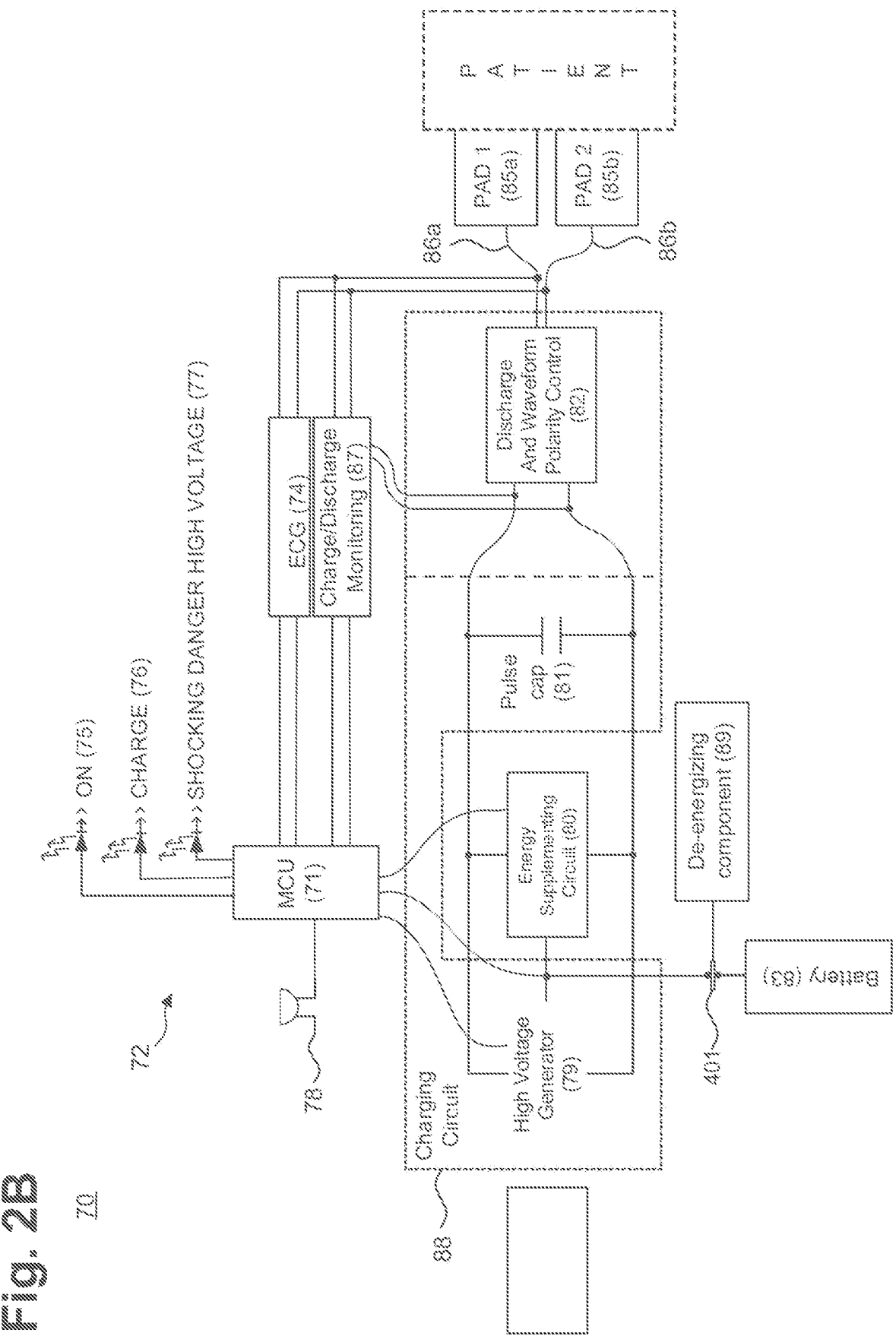

De-energizing the circuitry of the AED when the AED is not in use decreases the wear on the AED's electrical components and greatly extends their shelf life. Further, allowing such de-energized AEDs to be energized through intuitive user actions allows for quick deployment of such an AED. FIGS. 2A-2B are block diagrams showing functional components and a user interface 72 for a de-energizable defibrillation assembly 70 that includes a disposable pocketable AED in accordance with one embodiment. In the assembly 70, all of the components except the de-energizing component 89 described below are a part of the disposable pocketable AED (such as described below beginning with reference to FIG. 10). The de-energizing component 89 may be a part of the disposable pocket AED or may be at least in part external to the disposable pocketable AED. For the sake of subsequent clarity of the casing and pad deployment and use system, the defibrillation assembly 70 will be discussed in detail as both the casing innovation and the circuitry innovation are hand in glove coordinated.

The defibrillation assembly 70 includes components for providing a basic user interface 72 that includes a power switch (84) shown with reference to FIG. 2A. Alternatively, or in addition to the use of the power switch 84, the components providing a user interface include a piece of isolating material 401 positioned next to the battery 83, as shown with reference to FIG. 2B. In a further embodiment, both in the assembly described both with reference to FIGS. 2A and 2B as well as in other circuits described below, instead of the battery 83, another energy storage element could be used, such as an ultracapacitor or a hybrid battery. Other components of the user interface 72 include a "Power On Indicator" 75, a charging indicator 76, and optionally, a warning indicator 77 that indicates defibrillation shock delivery readiness with attendant dangers of exposure to high-voltage, plus an optional buzzer or speaker 78 through which audible instructions can be played. In one embodiment the user interface 72 also includes a visual display (not shown) on which text prompts can be displayed. In one embodiment, an AED incorporating the defibrillation circuit 70 can be semi-automatic and require the rescuer to manually trigger a shock by actuating the push to shock button (not shown); in a further embodiment, an AED incorporating the defibrillation circuit 70 employs a circuit to automatically deliver the defibrillation shock to the victim without user action once the charging circuit is ready, that is, the pulse capacitor is charged, and after the user has been warned to avoid any direct physical contact with the patient during shock delivery.

The delivery of power from the battery to other components of the assembly 70 can be entirely stopped while the AED is not in use, allowing the AED circuitry to be electrically unbiased during that time. A technique through which isolation of the battery can be accomplished is using an electromechanical component, such as the power switch 84 interfaced to the battery 83 (shown with reference to FIG. 2A) and preventing power from the battery 83 from reaching other components of the assembly 70 when the switch 84 is in an open position. The transition of the switch 84 to a closed position (in which power flows through the switch 84 to other components of the assembly 70) is caused by an activation of the de-energizing component 89 by an action of a user. As further described below, such action can include one or more of a changing configuration of a housing of the AED, such as through pressing of a user interfacing component like a button, as further described below, including with reference to FIG. 10; removing or manipulating an entirety or a part of an interchangeable or removable jacket (also referred to as a case in the description below) around the AED that includes the de-energizing component 89, including such as described below reference to FIGS. 20 and 21, though other kinds of cases are possible; changing a position of a mobile component of the AED, such as electrode pads or electrode pad packaging, as further described below, including with reference to FIG. 10. Further, at least a portion of the AED, or the case in which the AED is stored, can be covered in packaging (also referred to as 'wrapping' in the description below) prior to the AED being used, such as illustrated by FIG. 30. FIG. 30 is a diagram showing an AED 420 covered with a packaging 421 in which a de-energizing component 89 for activating the AED is embedded in accordance with one embodiment. Removing packaging from either the housing of the AED, another element of the AED (such as packaging on the electrode pads of the AED), or a case in which at least a portion of the AED is stored can activate the AED, though other actions actuating the de-energizing component 89 are possible.

The de-energizing component 89 includes the physical components whose position controls whether the switch 84 is in an open or a closed position. For example, in one embodiment, the switch 84 can be a magnetically triggered reed switch and the de-energizing component 89 includes a magnet whose field keeps the switch 84 in the open position when the AED is not in use. The magnetically triggered reed switch includes a pair of magnetically actuated contacts in a hermetically sealed envelope that are not in contact with each other when a strong enough magnetic field is present (and the switch 84 thus maintains an open position when the device is not in use) and that come into contact with each other (shifting the switch 84 into the closed position) when the magnetic field is removed. The user's actions in preparing the AED for use move the magnet far enough from the reed switch 84 to allow the switch 84 to transition into the closed position 84. For instance, as further described below, the magnet could be located in the housing of the AED, or jacket around the AED, being close enough within the housing to the reed switch 84 to keep the reed switch open 84. A change in the configuration of the housing or jacket around the AED, such as a pressing or sliding of a mechanical user-interfacing component of the housing (such as a button shown with numeral 235 in FIG. 10 below, a lever on a surface of the housing; a sliding mechanical electrical or electromechanical component that could be directly or indirectly connected to the magnet; a tear-away or disposable component that includes the magnet; or a rotating knob directly or indirectly connected to the magnet,) forming part of a de-energizing component, moves the magnet far enough from the reed switch 84 to allow the transition to the closed position of the switch 84. Similarly, the magnet could be located in a portion of the case, such as the cover (also referred to as lid) for the printed circuit board (PCBA) enclosure, or electrodes enclosure, of the AED and a removal or opening of that portion moves the magnet far enough away to allow the reed switch 84 to transition into the closed position. Likewise, the magnet could be located in a packaging 421 wrapped around at least a portion of the AED or a case of the AED such that the removal of the wrapping would move the magnet far enough to allow the reed switch 84 to transition into the closed position. Similarly, the magnet could be positioned on one of the mobile parts of the AED, such as a non-contact surface of the electrode pads, and the removal of the mobile part from the position occupied while the AED is not in use moves the magnet far enough to allow the reed switch 84 to transition into the closed position. In addition to the magnet, the de-energizing component 89 can include one or more mechanical links or interconnects (such as a plastic component, metal component, polymer component, alloy component, composite component, or a wire for example) to the magnet. For example, one end of a wire could be attached to a magnet within the housing of the AED while another end could be attached to an object on which the user takes action while preparing the AED for deployment, such as for the packaging of the AED, a cover of the case of the AED, or an electrode pad of the AED. The movement of the object by the user causes the wire to displace the magnet from the original position and thus allows the power switch 84 to transition into the closed position due to the pull of the wire. In a further embodiment, the de-energizing component 89 could include a button (or another mechanical user-interfacing component such as a lever, slide, knob, or tear-away or disposable component) on the housing of the AED that is mechanically interconnected to the magnet, with the pressing of the button causing the magnet to move far enough from the reed switch 84 to allow transitioning into the closed position. In another embodiment the magnet is a permanent, high-field strength, component and is positioned close enough to the reed switch 84 to prevent an accidental transitioning of the reed switch 84 into the closed position by other magnets that the AED can become proximate to in typical deployment settings. The magnet is made of a material that is resistant to changing the magnetic field due to external temperature fluctuations, or external magnetic fields. In one embodiment, the magnet can be a ceramic magnet, though in further embodiments other kinds of magnets such as alnico, ferrite, samarium cobalt, neodymium or neodymium iron borite are also possible. The magnet may also be a blend of plastic or other binding agent and a magnetic material to increase resistance to corrosion and mechanical failure.

In a further embodiment, the switch 84 can be a mechanical switch and the de-energizing component 89 can be mechanically connected to the switch 84, with the actuation of the de-energizing component 89 mechanically causing a shifting of the switch 84 into the closed position. For example, as described above, the de-energizing component 89 could include a mechanical link or interconnect, such as a wire, one end of which is connected to the mechanical switch 84 and another end of which is connected to an object that a user takes action on when preparing the AED for deployment, such as the packaging 421 of the AED, a cover (or another removable or movable part of the case, such as PCBA enclosure, or electrodes enclosure) of the case of the AED, or an electrode pad of the AED, with the movement of the object by the user causing a shifting of the mechanical switch 84 into the closed position due to the pull of the wire. Similarly, a change in a configuration of the housing of the AED (such as a pressing of a button or another mechanical user-interfacing component such as a lever) can cause the mechanical switch 84 to shift into the closed position due to a pull (or pushing) of mechanical interconnects connected to the button. Other ways for the de-energizing component 89 to actuate the mechanical switch are possible.

In a still further embodiment shown with reference to FIG. 2B, the de-energizing of the assembly 70 could be implemented using a piece of electrically isolating material inserted between the battery 83 and electrical connection to the components of the assembly 70 the battery 83 provides power to. While the piece of isolating material is shown as being shaped as a wedge 401 (and the piece of material is referred to as a wedge 401 in the description below) with reference to FIG. 2B, in a further embodiment, other shapes of the isolating material 401 are possible such as a film. The isolating material can be one or more of plastic, mylar, rubber, another non-conductive material, or a material that is covered with a non-conductive coating. The battery 83 is pushed against the wedge 401 (such as due to being in contact with compressed material which in turn pushes against the battery 83) and when the wedge 401 is removed, the battery 83 makes contact with the electrical connections to the rest of the assembly 70, allowing the battery 83 to power the assembly. The removal of the wedge 401 could be accomplished through multiple actions of the user on the de-energizing component 89. In one embodiment, the de-energizing component 89 could be integrally connected to the wedge 401, with the trigger protruding from the housing of the AED; the user could pull on the protruding de-energizing component 89 to remove the wedge 401 from the AED. Alternatively, the de-energizing component 89 could be connected to the wedge with one or more mechanical interconnects (such as a wire) and the user's actions on the trigger causes the removal of the wedge 401 due to being pulled (or pushed) via the interconnects. For example, as described above, the de-energizing component 89 could include a wire one end of which is connected to the wedge 401 and another end of which is connected to an object that a user takes action on when preparing the AED for deployment, such as the packaging of the AED, a cover of the case (or another movable or removable part of the case) of the AED, or an electrode pad of the AED, with the movement of the object by the user causing a removal of the wedge 401 from the initial position due to the pull by the wire. Similarly, a change in a configuration of the housing of the AED (such as a pressing of a button or another mechanical user-interfacing component such as a lever) can cause the removal of the wedge 401 from the initial position. The wedge 401 could also be connected to the mobile parts of the AED case, such as a lid, hinge, snap hook, and when opened or moved the insulating material is removed from between the battery 83 and the rest of the circuitry. Other ways for the de-energizing component 89 to cause the removal of the wedge 401 from the initial position (and consequently energizing of the assembly 70) are possible.

In a further embodiment, a single assembly 70 could include both the power switch 84 and an insulating wedge 401 located either between the power switch and the battery 83 (or another point in the electrical connections between the battery 83 and other components of the assembly 70). In this embodiment, a single trigger 83 could cause both the shifting of the power switch 84 into the closed position and the displacement of the insulating material 401 from the electrical path of battery power. Alternatively, multiple de-energizing components 89 could be included with the AED, with one de-energizing component 89 causing the shifting of the power switch 84 to the closed position and a second de-energizing component causing a displacement of the isolating wedge 401.

Figure 28:
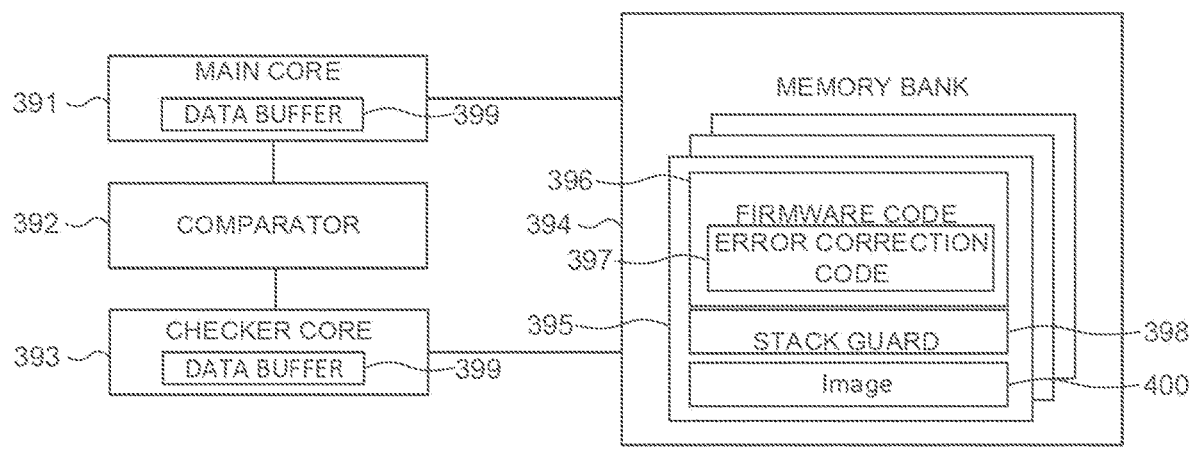
FIG. 28 is a block diagram showing the structure of the MCU in accordance with one embodiment.

The defibrillation circuit 70 is controlled by a microcontroller unit (MCU) 71, described in detail below with reference to FIG. 28, or system-on-chip controller (SOC) (not shown) that is programmable, which allows updated controller firmware to be downloaded from an external source into a persistent memory store. Sensing circuit 87 shown with reference to FIGS. 2A, 2B) is connected in parallel with the inputs and outputs of a discharge and polarity control circuit 82. The sensing circuit 87 determines the high-voltage capacitor charge level and captures the patient shock waveform and transmits it to the MCU 71. The defibrillation energy that is received from the pulse capacitor 81 as an input to the discharge and polarity control circuit 82 and the defibrillation waveform or "pulse" that is output is captured by the sensing circuit 87 and transmitted to the MCU 71. An ECG front end circuit 74 captures the heart rhythm and transmits the rhythm to the MCU 71. The ECG front end circuit 74 is connected in parallel with the leads 86*a-b* of the pair of electrode pads 85*a-b* to sense cardiac signals, while the sensing circuit 87 is connected in parallel with the discharge and polarity control module's input leads to monitor the shock delivery process. In a further embodiment, the MCU 71 interfaces to the sensing circuit 87 to continually measure patient impedance and adjusts parameters in the high-voltage generator module 79 and the low voltage energy supplementing module 80 to alter one or more of energy, voltage, and pulse width in real time, as further discussed infra with reference to FIG. 8. The ECG is transmitted to the MCU 71 where an algorithm makes a shock or no-shock decision. The algorithm is implemented through a conventional VF detection algorithm to detect the presence of a shockable rhythm, such as published by A. Fan, et al., Shockable Rhythm Detection Algorithms for Electrocardiogram in Automated Defibrillators, AASRI Conf. on Comp. Intel. and Bioinfor. pp. 21-26 (2012). The ECG front end circuit 74 is implemented optionally through conventional ECG analog front-end chips such as the ADS1x9xECG-FE family of integrated analog front-end ECG circuits, available from Texas Instruments, Dallas, TX. Other types and configurations of sensing and ECG front end circuitries are possible.

When a shockable rhythm is detected, based on inputs from the impedance sensing circuit (not shown), the MCU 71 determines the parameters of a defibrillation waveform in terms of energy, voltage, and pulse width; the defibrillation waveform is algorithmically selected based on the nature of the shockable rhythm to be medically appropriate for restoring normal cardiac rhythm. Up to a maximum of six shocks may be needed if the victim fails to be resuscitated, after which further shocks are generally futile.

In response to the ECG waveform the microcontroller or SoC 158 (shown with reference to FIG. 7) uses an algorithm to determine if a shockable rhythm is still present after initial shock delivery, that is, defibrillation failed to establish normal cardiac rhythm, the MCU 71 may simply repeat the delivery of the defibrillation pulse or, if appropriate, revise the parameters of the defibrillation waveforms for the subsequent pulses. In an alternative embodiment for such a situation, subsequent defibrillation shocks may need to be escalated in energy output or other waveform characteristics such as polarity are altered. In a further embodiment, parameters consisting of one or more of energy, voltage and pulse width are adjusted by the MCU 71 in real time, as further discussed infra with reference to FIG. 8.

In addition to reduction of computational errors due to the electrical components of the assembly 70 not being under bias when the AED is not in use, the structure of the MCU 71 can provide further safeguards against such errors. FIG. 28 is a block diagram showing the structure of the MCU 71 in accordance with one embodiment. The MCU 71 may optionally include lockstep processors that perform parallel processing: a main core 391 that controls the operations of other components of the assembly 70 and a checker core 393 that checks computations of the main core 391 before the main core 391 uses the results of those calculations to control the AED. Both the main core 391 and the checker core 393 are structurally identical and include an identical central processing unit. All of the computing operations that the main core 391 and the checker core 393 perform are identical and the results of these identical operations are compared by a comparator 392. If the answers for the identical operations performed by main core 391 and the checker core 393 do not match, indicating a computational error by either the main core 391 or the checker core 393, the comparator 392 notifies the main core 391 (and optionally the checker core 393). The main core 391 can take an action based on the mismatch, including one or more of rebooting the main core 391, the checker core 393, and possibly other components of the assembly 70 as well as repeating the operations whose results mismatched and commanding the checker core 393 to repeat the same operations, though other actions by the main core 391 are also possible. Thus, the chances of a computational error negatively affecting the performance of the AED are greatly reduced.

The MCU 71 further includes a memory bank 394 that includes one or more memories 395. At least some of the memories 395 further include firmware code 396 whose execution by the main core 391 controls the functioning of the AED. The firmware code 396 further includes error correction code ("ECC") 397. The ECC 397 can include parity bits, though other forms of ECC 397 are also possible. A parity bit is a bit added to a string of binary code that ensures that the total number of 1-bits in the string is even or odd. If the total number of 1-bits is different from what the number is supposed to be (such as due to a bit flip caused by cosmic radiation), the main core 391 would detect the difference as an error in the firmware code 396. In one embodiment, the main core 301 can correct the code upon the detection of the error using additional parity bits (that can help recover from a single bit error) or a backup. In a further embodiment, if the error is too complicated to identify using the parity bits, the main core 391 can reference an image 400 of the firmware code 396 that is stored in an additional memory region 395. The image 400 shows the code 396 as the code 396 was at the time of the manufacturing of the AED (or another point of time where no errors were present in the code 396) and comparing the code 396 in the memory 395 to the image 400 of the code 395 allows the main core 391 to identify what bits of the code are incorrect and correct the incorrect bits. Thus, the chances of an error in the firmware code 396 are greatly reduced. In one embodiment, a single image 400 could show the firmware code present in all of the memories 395. In a further embodiment, the memory bank 394 could store multiple images 400, with each of the images 400 showing the code 396 stored in one of the memories 395. The memories that can include firmware code 396 and ECC 397 include code flash memory, a data flash memory, a local ram memory, and a data transfer request memory, though other kinds of memories are also possible utilizing ECC 397. The main core 391 can execute multiple redundant error correction modules to further reduce the probability of such errors.

Further, the code flash memory 395 can include ECC 397 on the internal address bus connecting various components of the MCU 71 (and the assembly 70 overall) to which the main core 391 can send commands while controlling the AED; these addresses can also include parity bits to detect introduction of errors into the addresses. To further increase the accuracy with which the main core 391 addresses various components (and thus decrease rate of sending commands to wrong components), the MCU 71 can include peripheral bus guards (not shown) to detect out of range accesses.

Further, during execution of subroutines for controlling of the AED, the main core 391 (and the checker core 393) stores the stack data structure with information about active subroutines (the "call stack") in a data buffer 399. The overflow of the data buffer 399 (filling up of the data buffer 399 completely with data and then attempting to store more data in the data buffer 399) can cause a processor to execute undefined instructions. To avoid such an occurrence, both the main core 391 and the checker core 393 are interfaced to a stack guard 398, which is a memory space within the memory store 394 into which the main core 391 and the checker core 393 can store stack data if their respective data buffers 399 fill up.

In addition, the MCU 71 can include a plurality of security features to prevent tampering with the MCU 71. For example, the memory store 394 can be password-protected and the main core 391 and checker core 393 have to provide a password when accessing the memory store 394. Further, the main core 391 and the checker core 393 can each include a memory protection unit (not shown) that prevents unintended accessing of flash memory 395, RAM memory, and peripheral registers of the assembly 70. In addition, external access to the MCU 71 can be restricted through using a general purpose input/output (GPIO) safety register (not shown), which requires a password for access, as well as hardware tampering protections. Additionally, the MCU 71 can include hardware-based error detection, where an error detected by one of the peripheral parts of the MCU 71 (such as a serial port detecting that the port wrote incorrect data) is reported to the main core 391 and the main core 391 can take action regarding the error. In one embodiment defibrillation energy is generated through a combination of a modified conventional charging circuit 88 and optionally a low voltage energy supplementing module 80 which are synchronously controlled by the MCU 71. The charging circuit 88 includes a high-voltage generator module 79, which conventionally charges a high-voltage pulse capacitor 81 with energy that is stored for delivery as a defibrillation shock. The charging circuit 88 also includes a discharge and polarity control module 82, optionally in the form of an H-bridge, that switches in response to the sensing circuit 87, or, where the AED is semi-automatic, in response to the pressing of the "Shock" button or similar manual control, to deliver an appropriate defibrillation shock over the electrode pads 85a-b. Other configurations of switching elements in lieu of or in addition to an H-bridge are possible.

The discharge and polarity control module 82 interfaces over a pair of leads 86a-b to electrode pads 85a-b as outputs and to the pulse capacitor 81 as inputs. The H-bridge is formed with two "legs" on the output side containing the leads 86a-b for the electrode pads 85a-b and the other two "legs" on the input side electrically connected to a pulse capacitor 81. The discharge and polarity control module 82 is switchable to receive the defibrillation energy from the pulse capacitor 81, which is output by the discharge and polarity control module 82 as a defibrillation waveform or "pulse." In a further embodiment, the discharge and polarity control module 82 includes a polarity reversal correction circuit to ensure proper shock delivery in the event that the electrode pads 85a-b are improperly reversed. In a yet further embodiment, the polarity could automatically be reversed on the third defibrillation shock, as reversing polarity can aid in defibrillation of difficult cases.

In one embodiment, only a high-voltage energy generator 79 provides the energy to the pulse capacitor 81 for generation of the defibrillation waveform. Optionally, the assembly 70 can further include a low voltage energy supplementing module 80 that works as an adjunct to the high-voltage generator module 79 and generates supplementary defibrillation energy that is injected into the inputs of the pulse capacitor 81. The low voltage energy supplementing module 80 is electrically connected to the pulse capacitor 81 in line with the high-voltage generator circuit 79 and is constructed using one or more low voltage ultra-capacitors that store supplemental defibrillation energy. By virtue of having the low voltage energy supplementing module 80 effectively "on tap" to augment the defibrillation energy, the load on the pulse capacitor 81 is thereby lower when compared to the load required to charge a pulse capacitor in a conventional AED, which, in turn, enables the high-voltage generator module 79 and pulse capacitor 81 as used herein to be implemented with lower energy components. Furthermore, such lower energy components are well suited for use in an AED that is intended to be disposable and single use, where only a relatively reasonable degree of robustness is needed, and reusability is not required. In addition, these components lower the cost, size, and weight of the AED, enabling the AED to be packaged in a form factor, as described infra, that can readily fit into an average-sized pocket in a fashion analogous to contemporary mobile telephones.

The MCU 71 monitors the defibrillation waveform through the sensing circuit 87 and can adjust the supplemental energy stored by enabling and disabling the low voltage ultra-capacitors. A high-voltage step-up transformer is used by the low voltage energy supplementing module 79 to inject the stored supplemental defibrillation energy into the inputs of the pulse capacitor 81. This type of transformer can be packaged in a flat and thin planar design, known as a Planar Laminated High Energy Pulse Transformer, which is optimal for energy conversion efficiency and an ideal shape for a smartphone-like casing design. The low voltage energy supplementing module 80 uses a set of ultra-capacitors (or possible a single ultra-capacitor) in the range of 2.5V-48V and stores an amount of energy needed or to supplement a defibrillation pulse. The amount of supplementation varies depending on the application and target parameters of the device. The energy stored on the low voltage circuit could be as low as 10J, or as high as 3 times the full defibrillation energy. The low voltage energy supplementing module 80 additively contributes to the energy generated by the high-voltage generator module 79.

Figure 3:
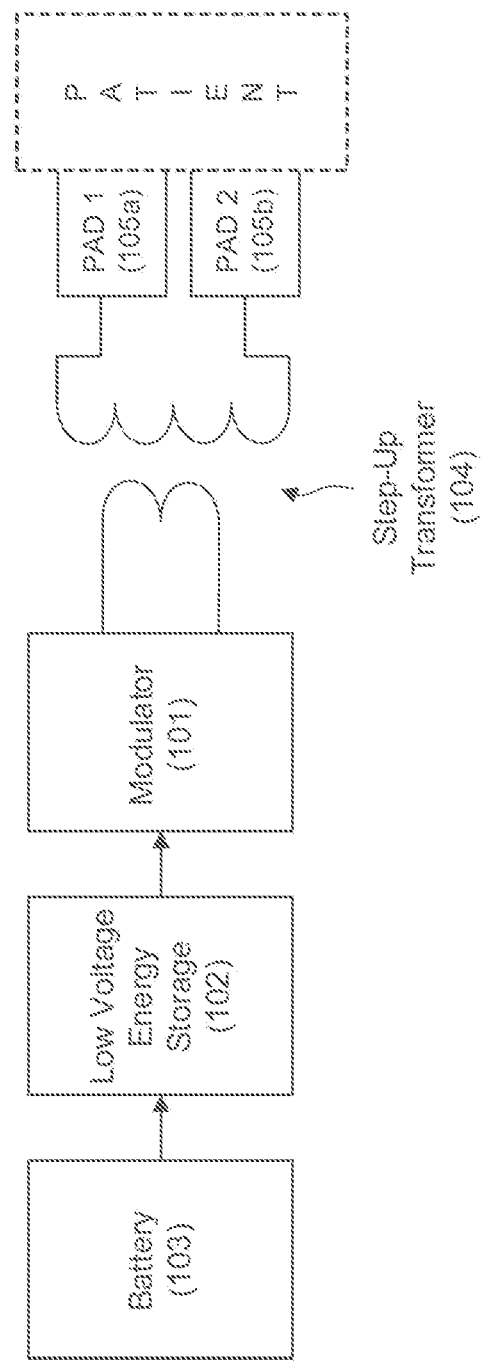
FIG. 3 is a schematic and block diagram showing a low voltage energy storage circuit for generating defibrillation waveforms energy in accordance with a further embodiment.

In one embodiment, the assembly 70 does not utilize low voltage energy for generating defibrillation waveforms, and only high voltage energy storage is used for this purpose. In a further embodiment, in which low voltage energy storage is utilized, low voltage energy storage for generating or supplementing defibrillation waveforms can be achieved through several circuits, as discussed with reference to FIGS. 3-7. While described in the context of use in personal AEDs, these low voltage high-energy storage circuits are adaptable for use in hospital defibrillators and in medic vehicle defibrillators as well as in implantable defibrillators. In its simplest form, energy is stored at a low voltage and switched through a step-up pulse transformer to generate the necessary defibrillation waveform, such as the biphasic waveform 181 (shown in FIG. 8). FIG. 3 is a schematic diagram showing a low voltage energy storage circuit 100 for generating defibrillation energy waveforms in accordance with one embodiment. Except as otherwise noted, the sensing and ECG circuits are omitted for clarity.

Here, the defibrillation circuit 100 includes four basic components, a pulse optimized step-up transformer 104 that feeds the defibrillation energy to a pair of electrodes 105a-b. The transformer 104 is driven by a modulator (or load switch) 101 that is fed by a low voltage energy storage module 102 containing one or more low voltage ultra-capacitors. Power is supplied by a battery 103. This circuit is completely open loop and relies upon pre-computed timing control pulses to instantiate the defibrillation waveform. In addition, this circuit is simple and therefore low cost.

Figure 4:
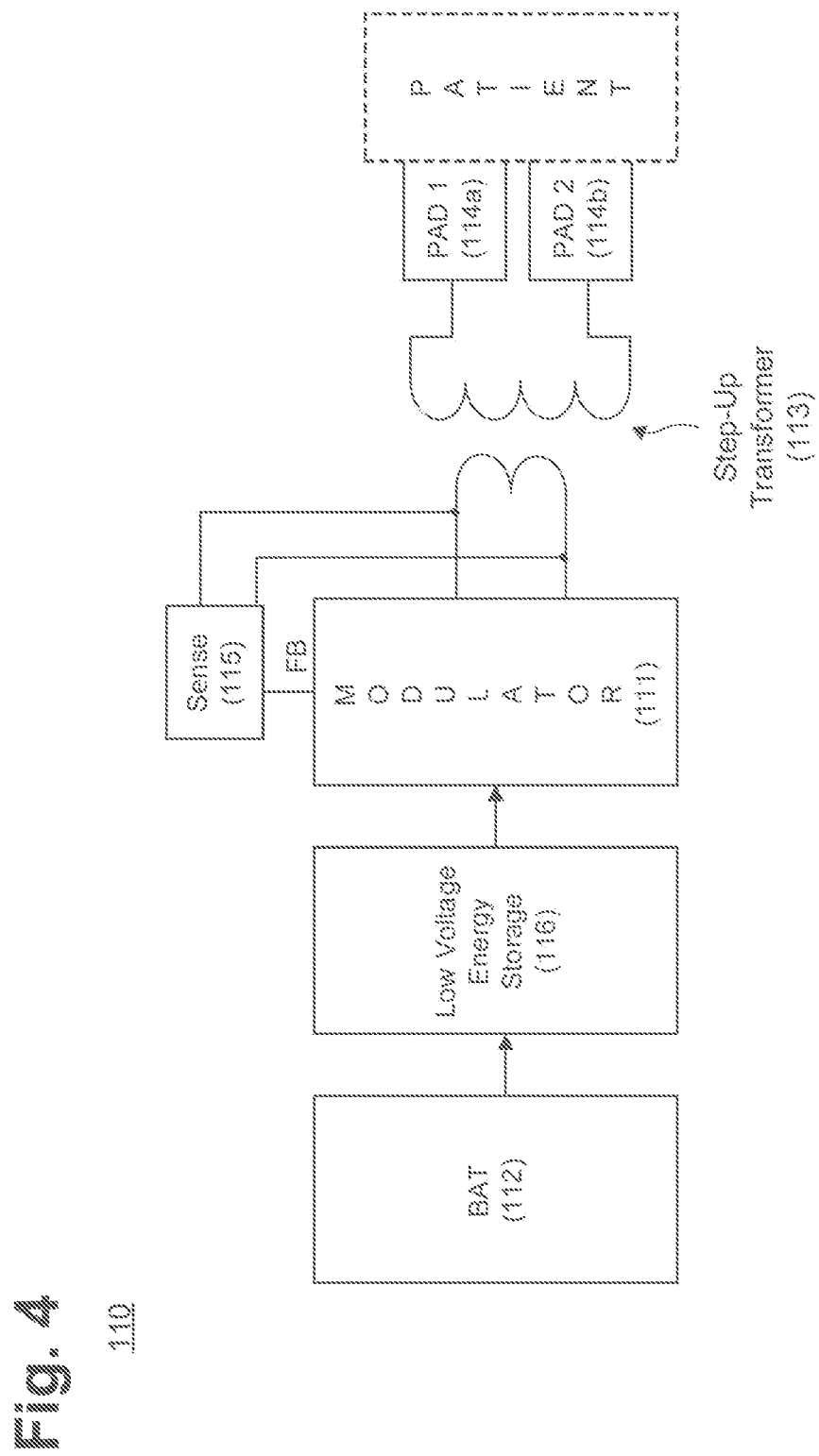
FIG. 4 is a schematic and block diagram showing a low voltage energy storage circuit for generating defibrillation waveforms energy with feedback in accordance with a further embodiment.

In another embodiment the electrical stimulus delivered to the patient can be monitored and inferred through current sensing employed on the primary side of the high-voltage pulse transformer. FIG. 4 is a schematic diagram showing a low voltage energy storage circuit 110 for generating defibrillation energy waveforms with feedback in accordance with a further embodiment. As before, the sensing and ECG circuits are omitted for clarity except as otherwise noted.

Here, the defibrillation circuit 110 includes four basic components, a pulse optimized step-up transformer 113, which serves to convert low-voltage high current energy to a high-voltage defibrillation pulse. A switch or modulator (or load switch) (111) to excite the high-voltage pulse transformer that feeds the defibrillation energy to a pair of electrodes 114a-b. The transformer 113 is also driven by low voltage energy storage module 116 that generates supplementary energy through a bank of ultra-capacitors that are fed to the inputs of the transformer 113. Power is supplied by a battery 112. Additionally, a sensing module 115 includes sensing leads through which to monitor the inputs of the transformer 113, which is used by the sensing module 115 as feedback for switching the bank of ultra-capacitors, as required. The feedback is fed into a modulator (or load switch) 111 that controls the stimulus to the high-voltage pulse transformer 113, which results in better control and regulation of the energy delivered to the patient regardless of patient impedance.

Figure 5:
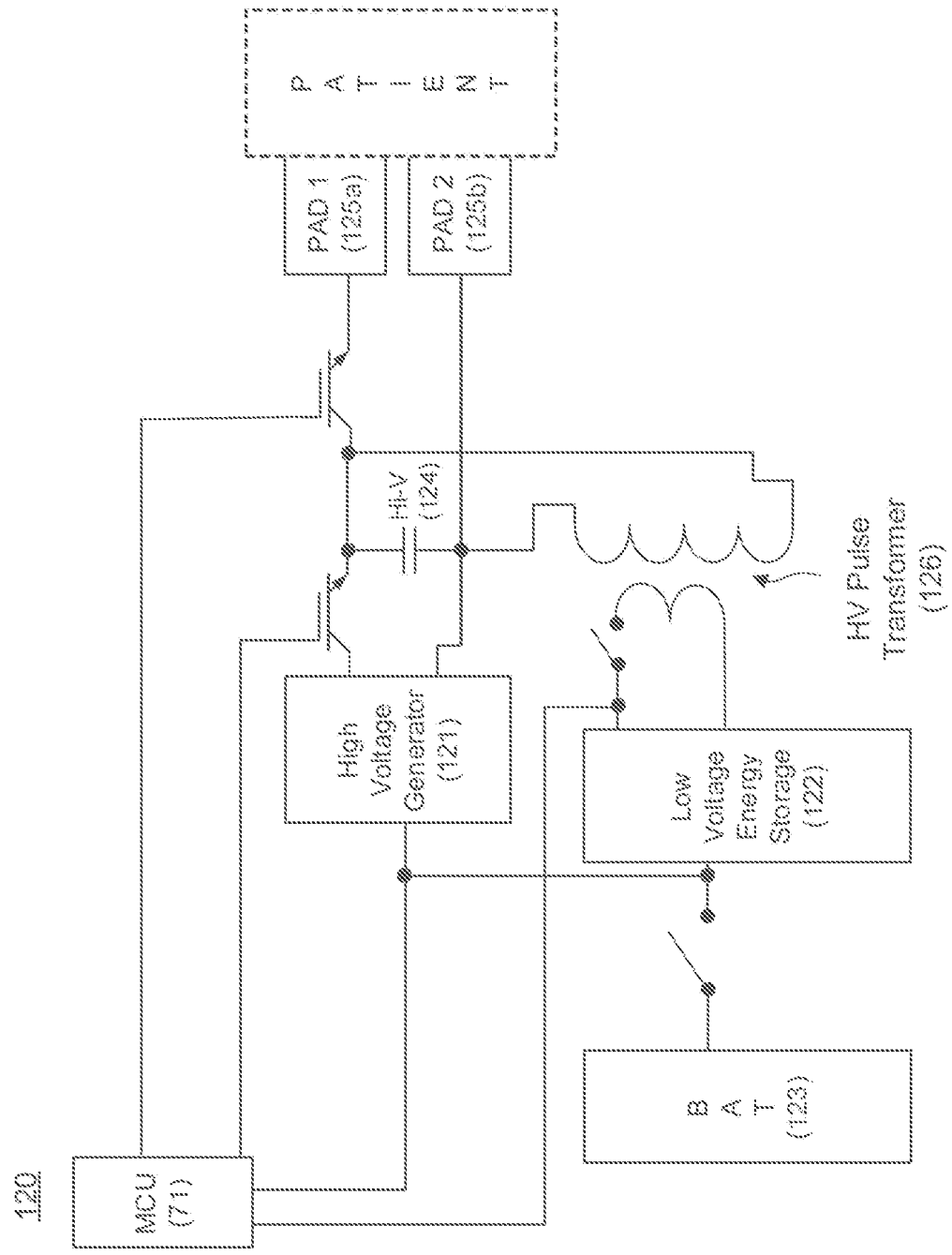
FIG. 5 is a schematic and block diagram showing a hybrid low voltage energy storage circuit for generating defibrillation waveforms energy in accordance with a further embodiment.

A hybrid energy sourcing approach can be taken by pre-charging a high-voltage capacitor in addition to a low-voltage pulse capacitor (or ultra-capacitor with pulse discharge capabilities). FIG. 5 is a schematic diagram showing a hybrid low voltage energy storage circuit 120 for generating defibrillation energy waveforms in accordance with a further embodiment. As before, the sensing and ECG circuits are omitted for clarity except as otherwise noted. Further, while a power switch 84 is shown, as described above, flow of power from the battery 83 could also be controlled using an insulating wedge 401 or another electro-mechanical implementation.

The defibrillation circuit 120 includes three basic components, a high-voltage generator (HVG) circuit 121, which serves the purpose to charge a high-voltage capacitor 124 that feeds the defibrillation energy to a pair of electrodes 125a-b. The high-voltage generator boost circuit 121 is supplemented by a low voltage energy storage (LVES) circuit 122 coupled through a high-voltage pulse transformer 126 that generates supplementary energy that is fed to the electrodes 125a-b. Power is supplied by a battery 123 through a switch. During discharge, some energy is supplied by the high-voltage capacitor 124 while additional energy is discharged into the patient from the LVES circuit 122 through the high-voltage pulse transformer 126. As the defibrillation energy is supplied by multiple sources, tradeoffs can be made between magnetic pulse transformer size and capacitor size, optimizing for the best available technology at the time. In this implementation, there is no control and feedback in the defibrillation pulse, which is a trade-off favoring simplicity and clinically reasonable efficacy versus complexity in favor of the appearance of perfection, albeit not the reality of it.

Figure 6:
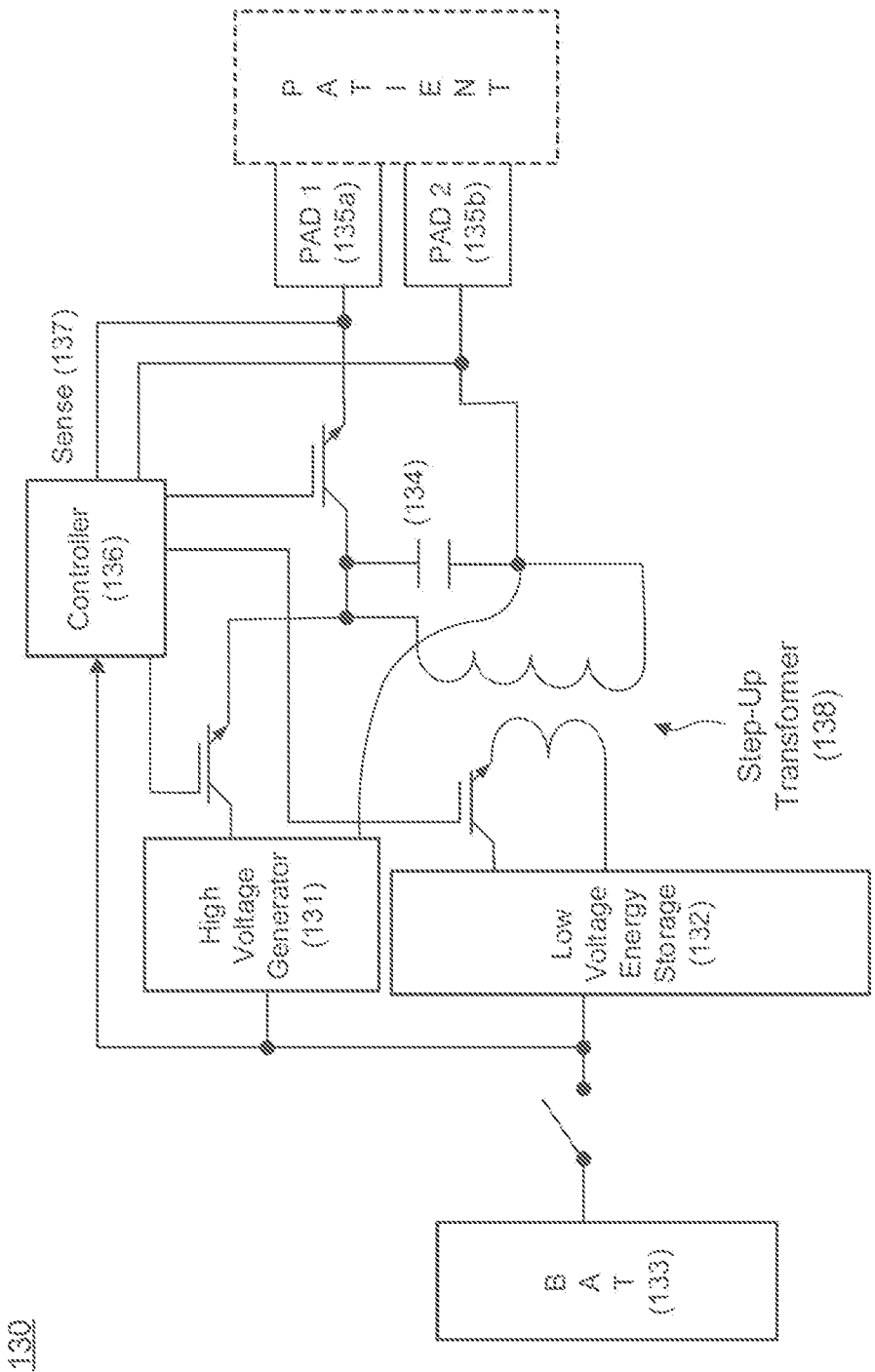
FIG. 6 is a schematic and block diagram showing a hybrid low voltage energy storage circuit for generating defibrillation waveforms energy with feedback in accordance with a further embodiment.

The foregoing hybrid energy delivery approach can be expanded upon with a controller that senses the therapy being delivered to the patient which allows active control and optimization of the defibrillation waveform depending on real-time impedance feedback. FIG. 6 is a schematic diagram showing a hybrid low voltage energy storage circuit 130 for generating defibrillation waveforms energy with feedback in accordance with a further embodiment. As before, the sensing and ECG circuits are omitted for clarity except as otherwise noted. Further, while a power switch 84 is shown, as described above, flow of power from the battery 83 could also be controlled using an insulating wedge 401.

Here, the defibrillation circuit 130 includes four basic components, a high-voltage generator (HVG) circuit 131, which similarly serves to charge a high-voltage capacitor 134 that feeds the defibrillation energy to a pair of electrodes 135a-b when defibrillating. The low voltage energy storage (LVES) circuit 132 is supplemented by a bank of ultra-capacitors connected through a step-up pulse transformer 138 that generates supplementary energy that is fed to the inputs of the H-bridge. Power to the system is supplied by a battery 133. Additionally, a controller 136 includes sensing leads 137 through which to monitor the patient and the energy delivered. This waveform is used by the controller 136 as feedback for switching the bank of ultra-capacitors on and off to deliver supplementary energy as required. The controller 136 can modify the amount of energy being transferred to the patient in real time by shutting off or activating the low voltage storage element delivering additional energy to the patient only when needed resulting in a more accurate and efficacious defibrillation waveform. Long-duration defibrillation pulses, that is, a waveform with a duration much greater than 20 milliseconds (msec), can be counter-productive, as can occur in select patients with high resistance and impedance to current delivery and may in fact impede defibrillation or induce re-fibrillation. Contrarily, ultra-low resistance patients, such as small children, can manifest too brief of a defibrillation waveform, that is, a waveform with a duration of less than 4 msec, perhaps also impeding defibrillation efficiency.

Figure 7:
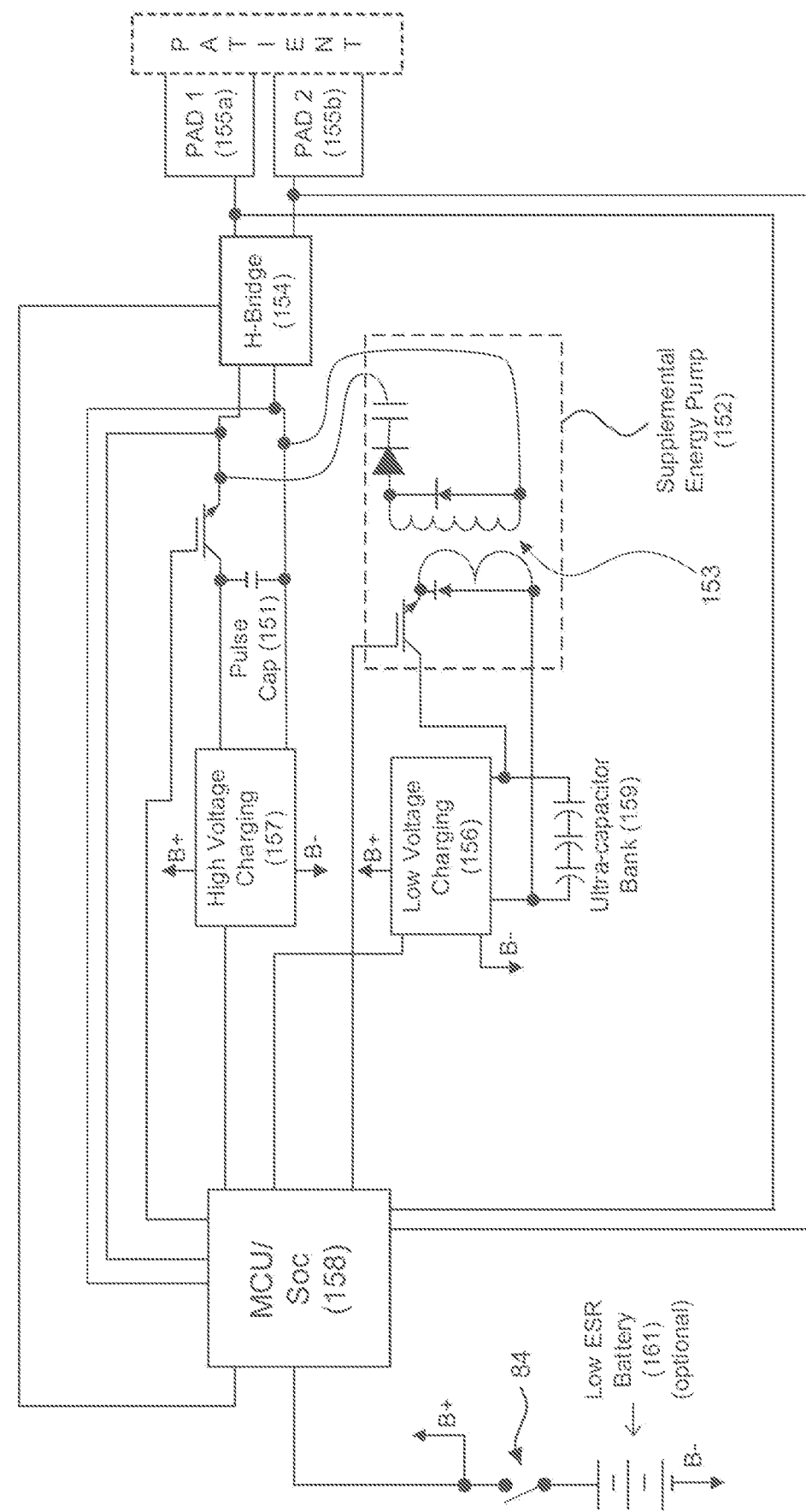
FIG. 7 is a schematic diagram showing a hybrid low voltage energy storage circuit for generating defibrillation waveforms energy with feedback and supplemental energy pump in accordance with a further embodiment.

The foregoing hybrid energy delivery approach with feedback can be improved upon with the addition of a supplemental energy pump. FIG. 7 is a schematic diagram showing a hybrid low voltage energy storage circuit 150 for generating defibrillation waveforms energy with feedback and supplemental energy pump 152 in accordance with a further embodiment. The circuit 150 is controlled by a microcontroller (MCU) or system-on-chip (SOC) 158 (hereafter, simply "MCU"). While a power switch 84 is shown, as described above, flow of power from the battery 83 could also be controlled using an insulating wedge 401.

The supplemental energy pump 152 is able to dynamically couple energy stored in an optional low voltage charging module 156 into the patient through a transformer 153 incorporated into the supplemental energy pump 152 with high-voltage stored in a high-voltage charging module 157. This approach provides superior control of the energy delivery and waveform. The pumping action decreases the dielectric withstand voltage requirements and step-up transformer sizing requirements required by the hybrid low voltage energy storage circuit 150; thus, the respective breakdown voltage and voltage increase can be significantly lower here when compared to a conventional AED intended for long term reusability, that is, non-disposable multiple victim use. In turn, lower voltage and capacitance components can be safely used throughout the hybrid low voltage energy storage circuit 150, including a lower capacity power source. Moreover, given the dynamic nature of the circuit, the circuit 150 is capable of high efficacy on a wide variety of patients and allows additional flexibility for the internal components to be selected to optimize for cost, size, and weight. This approach also features an optional H-bridge 154 coupled output to further simplify the generation of a biphasic pulse or correct for incorrect (reversed) placement of the electrodes 155a-b.

As with conventional AEDs, defibrillation energy is stored in a pulse capacitor 151, which can be the largest component and the one requiring specific housing considerations as discussed infra. A high-voltage charging module 157 conventionally increases voltage drawn from a battery 161 with a low equivalent series resistance (ESR) rating, drawn through a rectification circuit (not shown) to convert the energy into DC, which is then stored in the pulse capacitor 151. However, the low voltage charging module 156 is coupled to a bank of ultra-capacitors 159, which only need to be rated to handle modest low voltages in the range of 2.5V-48V with a capacitance range yielding up to 360J, which would be in the range of 96 Farads (F) for 2.5V and 0.26 F for a voltage of 48V. The bank of ultra-capacitors 159 is preferably arranged in series, series-parallel or parallel configurations to store up to 360J of energy or more.

The supplemental energy pump 152 is enabled by the MCU 158 when the H-bridge 154, if present, is discharging energy into the patient to maintain the defibrillation shock for several milliseconds; the bank of ultra-capacitors 159 have a high discharge rate that allows the low voltage charging module 156 to additively augment the defibrillation energy during shock delivery. The supplemental energy pump 152 allows the pulse energy to be stepped up during delivery by interfacing with the H-bridge's input leads. The MCU 158 can monitor the supplementing energy being delivered by the low voltage charging module 156 over a pair of sensing connections that interface with the H-bridge's output leads.

With this form of energy supplementation, a lower rated high-voltage pulse capacitor 151 can be used than found in conventional AEDs, and, given the expected disposable single use operation of an AED using the hybrid low voltage energy storage circuit 150, the circuit 150 can be powered using a low cost and lightweight battery 156, rated in the range of 2.5V-48V. In turn, the use of such a small form factor battery allows an AED using the hybrid low voltage energy storage circuit 150, such as discussed with reference to FIGS. 10-18, to be both disposable and carriable in an average pocket presuming innovations in accompanying housing considerations as later described. In a still further embodiment, an AED using the hybrid low voltage energy storage circuit 150 includes a battery charging circuit (not shown) with which to recharge the battery 161. A similar component rating reduction of the pulse capacitor circuit would be applicable where the foregoing circuits are adapted for use in a non-portable clinical-grade defibrillator and in an implantable defibrillator, the latter of which could also benefit from a battery supply rating reduction.

A disposable pocketable AED using the hybrid low voltage energy storage circuit 150 is intended to be available 24/7/365 and easy to use with little to no training required. FIG. 8 is a flow chart showing a method 170 for operating a disposable pocketable AED in accordance with one embodiment. To start, the MCU 71 determines whether the AED has been activated by the user by taking action on the de-energizing component 89 or whether the inflow of power to the MCU 71 is accidental. The determination can be based on the length of time during which the MCU 71 receives the power from the battery 83. For example, if the AED was accidentally dropped, the fall may temporarily dislodge the magnet holding the switch 84 in open position, with the magnet returning to the original position immediately after the fall. In that case, the MCU 71 will receive power from the battery only for a short time and based on the length of the time the power is received falling below a threshold, the MCU 71 can detect the power inflow as accidental and not due to the AED being activated by the user. If such accidental activation is detected, the method 170 moves to step 180, with the MCU 71 controlling the discharge and powering down of the AED. Other ways to detect an accidental activation are possible.

Figure 29:
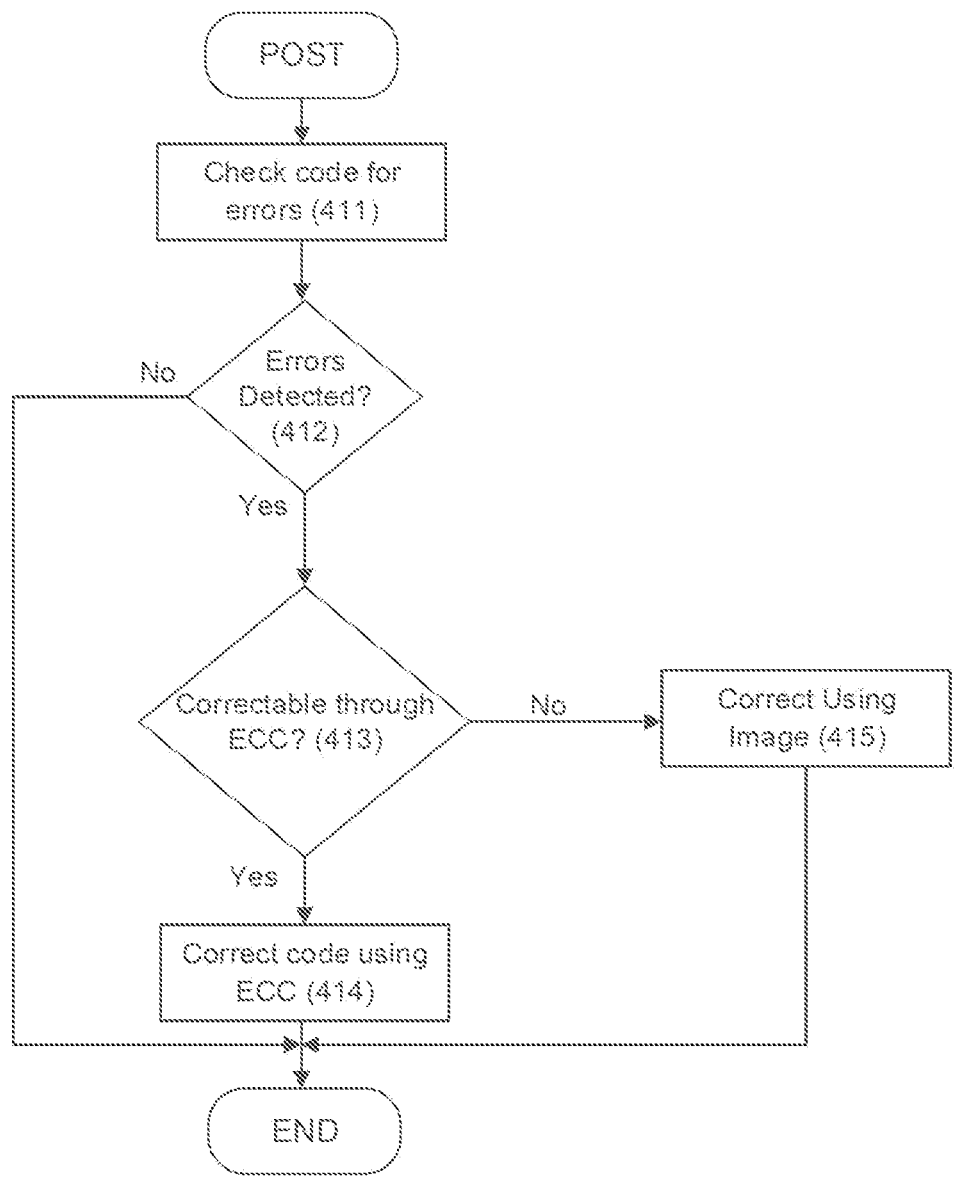
FIG. 29 is a flow diagram showing a routine for correcting code errors for use in the method of FIG. 8 in accordance with one embodiment.

If the activation of the AED by the user is detected (step 171), the MCU 71 optionally may perform a power-on self-test (POST), which optionally includes diagnostic checks, including checking for and correcting errors in the firmware code 396 used by the MCU 71, as further described in detail with reference to FIG. 29 (step 172). In a further embodiment, the main core 391 can check for code errors at other times during the execution of the method 170.

Following successful POST (power on self-test) (step 172), a record of the AED's activation is made in an onboard log (step 173) and the pulse capacitor is pre-charged to a conservative level (step 174), by the high-voltage charger module and optionally by the low voltage energy storage circuit, as further described below with reference to FIG. 9. However, in a further embodiment, the record can be generated after the activation (171), while the charge is initiated after POST (172). The state of the electrode pads is determined, and the methodology only proceeds once the pads are applied (step 175) as further defined infra. The AED detection algorithm determines whether a shockable rhythm is present (step 176).

Provided a shockable rhythm is sensed (step 176), the AED issues a warning to the user (step 177) and a defibrillation shock is delivered (step 178). The defibrillation shock is delivered as a high-voltage therapeutic waveform 181, preferably as a biphasic waveform, such as a biphasic truncated exponential (BTE), pulsed biphasic, and rectilinear biphasic waveform, modified biphasic, arbitrary or, alternatively, as a monophasic waveform. Other defibrillation waveforms are possible. Once the shock has been delivered, the device determines whether a normal rhythm has been restored and, if so, the methodology is done (step 179) and the AED will discharge any remaining energy in the pulse capacitor or low energy supplementing circuit and power down (step 180) after up to 30 minutes of a non-VF rhythm. In some cases, several defibrillation shocks are required with the AED delivering biphasic defibrillation shocks. Typically, 150 J biphasic shocks are delivered and may be delivered up to 6 times if needed. In an alternative embodiment, the initial energy level for defibrillation begins at or around 120 J and either repeats or escalates for the second and subsequent defibrillation shocks up to a maximum of at or around 360 J. In the use of escalation, the defibrillation energy is automatically adjusted by the AED with each subsequent defibrillation shock. In a further embodiment, the polarity of the defibrillation shock is reversed on the third shock (or any subsequent shock following the first shock) should no restoration of a non-shockable rhythm occur. In a further embodiment, the AED can automatically limit the number of shock re-attempts permitted, as after three defibrillation shocks, resuscitation of the victim 18 becomes unlikely.

In a further embodiment, as part of the process of delivering the defibrillation shock (step 178), the AED measures patient impedance during application of the defibrillation shock through the sensing circuit and adjusts one or more of the energy, voltage, and pulse width of the defibrillation waveform 181 in real time to generate optimal defibrillation therapy, where the x-axis represents time (T) and the y-axis represents voltage (V). Knowledge of patient impedance is crucial in a traditional design, which is used to determine the energy required to pre-charge the high-voltage pulse capacitor to an appropriate level and to aid in realizing an appropriate energy deliver waveform. In practice, patient impedance changes during the shock, so conventional impedance-based pre-charge circuits have limited usefulness in achieving effective defibrillation. For instance, the impedance of a ten-year-old child is around 20 Ohms, whereas a 200-pound, middle-aged male typically has an impedance of about 75 Ohms. For both individuals, a waveform of 5-15 msec is likely necessary for effective defibrillation but their defibrillation pulse timing, and pre-charge parameters are different. Moreover, impedance on the skin's surface typically decreases as defibrillation therapy progresses. Thus, MCU 71 (shown in FIG. 2) interfaces to the sensing circuit to continually measure impedance in real time and adjusts parameters in the high-voltage energy delivery module 79 and optionally the low voltage energy supplementing module 80 to alter energy, voltage, and pulse width (duration). Other parameters are possible.

For instance, an exemplary biphasic waveform is defined with an asymmetrical 65% tilt from a leading-edge voltage $V_L$ and trailing edge voltage $V_T/-V_T$ with a polarity reversal halfway through the waveform. Patient impedance can affect the duration of the waveform where increased impedance means longer pulse width, lower voltage, or less energy to the heart, and decreased impedance means shorter pulse width, higher voltage, or more energy to the heart (unless patient impedance changes after the impedance is sensed). The most efficacious way to ensure correct energy delivery is to monitor and adjust the therapy in real time. One or more of these parameters can be adjusted by the MCU in real time to alter the amount of primary or supplementary energy contour of the shock to reflect the ideal target therapy represented by the biphasic waveform.

Checking for errors in the firmware code of the AED can reduce potential performance errors of the AED. FIG. 29 is a flow diagram showing a routine 410 for correcting code errors for use in the method 70 of FIG. 8 in accordance with one embodiment. Initially, the main core 391 checks for errors in the firmware code 396 using the error correction code 397, such as parity bits (step 411). If no errors are detected (step 412), the routine 410 ends. If one or more errors are detected (step 412), whether the errors are correctable using the error correction code 397 (such as parity bits) is determined (step 413). If the specific errors are identifiable and correctable using the error correction code 397 (step 413), the errors are corrected by the main core 391 based on the error correction code 397 (step 414), ending the routine 410. If the errors are too complicated to correct using the error correction code 397 (step 413), the main core 391 references the image 400 of the firmware code to make the correction (step 415), ending the routine 410.

The AED can optionally utilize low voltage energy storage to supplement the defibrillation circuit's pulse capacitor. FIG. 9 is a flow chart showing a charging routine 190 for use in the method 170 of FIG. 8. The primary and supplementary defibrillation energy is based on a high-voltage therapeutic waveform, such as the biphasic waveform shown in FIG. 8, which can be maintained by the microcontroller 71 (shown in FIG. 2) in its memory store. In a further embodiment, the AED measures patient impedance during application of the defibrillation shock and adjusts one or more of the energy, voltage, and pulse width of the defibrillation waveform 181 in real time to generate optimal defibrillation therapy and, in a still further embodiment, the AED can revise the optimal defibrillation therapy during the second and, if needed, third defibrillation pulses in the event that earlier defibrillation attempts have failed to restore normal cardiac rhythm. During charging of the pulse capacitor (step 191), the microcontroller compares the primary defibrillation energy and the supplemental energy (if any is used) to the energy required to deliver the defibrillation waveform 181. If the charging of the pulse capacitor is happening either too fast or too slow (step 192), as based on a plot of an expected slowest charging rate 196 and a plot of an expected fastest charging rate 197, a failure condition exists (step 193). The charging rate can be bounded, for instance, based on a pair of thresholds that respectively define upper and lower bounds of charging rate, such that a charging rate that exceeds the upper bound is considered too fast and a charging rate that falls below the lower bound is considered too slow. A failure condition in the expected charging rate can be useful in identifying potential problems with the charging circuit. An overly fast charging rate could indicate that capacity of pulse capacitor has decreased and may not have enough energy to perform its function when fully charged. An overly slow charging rate falling below the lower bound could indicate an excessive energy leakage in the circuit, which typically ends up being expressed as heat. In both charging rate plots, the x-axes represent time, and the y-axes represent voltage. Otherwise, charging continues until the circuit is charged (step 194), after which the microcontroller maintains and adjusts the charge in the pulse capacitor as needed (step 195).

FIG. 10 is a front view showing a disposable single use pocketable AED with dual free-floating electrodes in accordance with one embodiment. The AED 230 combines a highly portable form factor with high and low voltage energy storage circuits that deliver defibrillating energy out of only modest lightweight battery capacity that is isolated from the defibrillation pads. The AED 230 can advantageously use low voltage energy storage, as discussed supra with reference to FIG. 2 et seq., to supplement the high-voltage charger circuit used to charge the pulse capacitor. This innovation allows the circuit to be powered with a low cost and lightweight battery more suitable to the housing or case. Further, the high-voltage charger circuit and pulse capacitor can be down-rated from the high capacitance levels utilized in conventional designs, all of which significantly decreases cost and size, thereby making single-use and device disposability possible and, importantly, a pocket size, AED.

The AED 230 is housed in a small lightweight housing 231, about the size and weight of a mobile telephone, that is, in the range of 2.25 to 3.625 inches wide, 5.25 to 7 inches tall, and 0.25 to 1.875 inches deep and a weight in the range of 130 to 945 grams. Other sizes and form factors are possible. The pair of free-floating electrodes 232*a-b* (also referred to as pads elsewhere in the specification) are connected to the housing 231 by a pair of flexible leads 233*a-b*. A planar laminated high energy pulse transformer is incorporated into each electrode 232*a-b*, as further discussed infra with reference to FIG. 19. Each electrode 232*a-b* is coated with an adhesive hydrogel that ensures proper contact with the victim's skin. The electrodes 232*a-b* are for a single patient use only. The front of the AED 230 can include a user interface 234 designed to optimize user understanding that includes a set of visual instructions 237. Optionally, the AED 230 can be equipped with an alternative embodiment including a speaker (not shown) to generate voice prompts. A de-energizing component 89 for activating the AED 230 can also be located on a surface of one of the electrodes that does come into contact the patient. Optionally, mechanical interconnects (not shown) can extend from the de-energizing component 89 into the inside of the housing 231 of the AED, such as through being attached to one of the flexible leads 233*a-b*, while the electrodes 232*a-b* are outside the housing 231. Thus, the movement of the electrode 232a-b to which the de-energizing component 89 is attached from the position in which the electrode 232a-b was stored will cause the activation of the AED, either through the shifting of the power switch 84, removing the isolating wedge 401 from the path of power from the battery 83 to the rest of the assembly 70, or both. Alternatively, if the electrode 232a-b is stored inside the packaging, the de-energizing component 89 can be embedded in the packaging surrounding the electrode 232a-b and both the removal of the packaging and the movement of the electrode 232a-b will activate the AED 230. If multiple de-energizing components 89 are used, location of the de-energizing component 89 on both one or both of the electrodes 232a-b and on the packaging are possible.

The AED 230 includes a streamlined and simple user interface that facilitates understanding and proper use during an emergency by family or friends who may be confused and frightened by the SCA of someone they know. Once the AED is activated, such as through pushing, moving, unhooking, sliding, or lifting a user interfacing component 235 forming part of the de-energizing component 89, the status of the AED 230 is intuitively provided by a visual indicator 236 that changes color depending upon the state of the AED, for instance, through a display of "red," "yellow" and "green" to respectively indicate device activated but not attached to the patient, device attached and pulse capacitor charging, and a ready-to-shock condition. Other colors, forms and types of indicators are possible. In a further embodiment, the AED 230 includes mobile communications capabilities by which to automatically summon medical assistance, generally by calling 9-1-1 or the equivalent in most localities, upon the sensing of a shockable rhythm. The mobile communications capabilities integrated into the AED 230 by including appropriate circuits and components or through a special features module providing the mobile communications capabilities to the AED. The AED could also receive mobile communications capabilities through a wireless interface, such as WiFi or Bluetooth, over which the AED can communicate to a mobile phone or wide area network, such as the Internet, and relay a 9-1-1 call. Alternatively, a mobile phone or device could be supplemented with the features of the AED 230.

FIG. 11 is a cut-away view showing block component groups contained within the disposable single use pocketable AED 230 of FIG. 10. The AED's circuit is provided on a printed circuit board (PCB) 240 contained within the housing 231, which also contains a low-cost, high-energy density battery 238 (optionally, a primary cell) and a pulse capacitor 239.

FIG. 12 is a side view showing the disposable single use pocketable AED 230 of FIG. 10 with the housing and dual free-floating electrodes stowed in a carrying case 242 whose opening can be of several means, such as described in detail below with respect to FIGS. 12-27. The AED 230 is intended to be easily carried in a pocket and could be carried in a purse, backpack, glovebox, golf bags, and so forth, or on a refrigerator door, so as to enable the AED 230 to be conveniently on-hand in case of an SCA situation in the same manner that most people have their mobile phone on-hand.

FIG. 13 is a side view showing the disposable single use pocketable AED 230 of FIG. 10 with the housing and dual free-floating electrodes partially deployed from the carrying case 242. The pair of free-floating electrodes 232a-b share a similar front profile with the housing 231. The housing 231 and electrodes 232a-b slide out of the carrying case 242 when being deployed.

FIG. 14 is a back view showing the cable management system 241 of the disposable single use pocketable AED 230 of FIG. 10. A cable management system 241 is used to store the leads 232a-b inside of the housing 231, where the leads are internally retracted by the smart cable management system 241 until needed.

Figure 15:
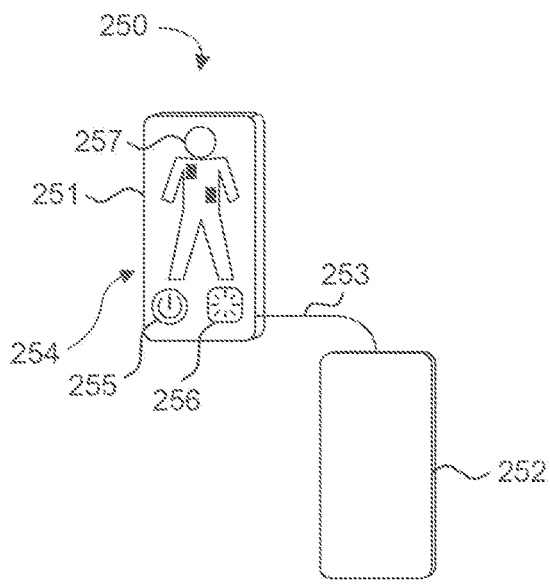
FIG. 15 is a front view showing a disposable single use pocketable AED with a single free-floating electrode in accordance with one embodiment.

One of the dual free-floating leads 232a-b can be eliminated by providing an electrode pad surface on the AED's housing. FIG. 15 is a front view showing a disposable single use pocketable AED 250 with a single free-floating electrode 252 in accordance with one embodiment. As before, the AED 250 is housed in a small lightweight housing 251, but only one free-floating electrode 252 is connected to the housing 31 by a single flexible lead 25.

Figure 16:
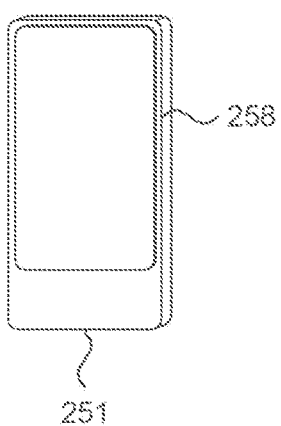
FIG. 16 is a rear view showing the integrated electrode of the disposable single use pocketable AED of FIG. 15.

FIG. 16 is a rear view showing the integrated electrode 258 of the disposable single use pocketable AED 250 of FIG. 15. An integrated electrode pad 258 is provided on a rear-facing surface of the housing 251. A planar laminated high energy pulse transformer is incorporated into each electrode 252, 258, as further discussed infra with reference to FIG. 19. Both the single free-floating electrode 252 and integrated electrode 258 are coated with an adhesive conductive hydrogel that ensures proper contact with the victim's skin. The front of the AED 250 similarly has a user interface 254 designed to optimize user understanding that includes a set of visual instructions 257. Optionally, the AED 250 can be equipped with a speaker (not shown) to generate voice prompts. Power is again controlled by an "On" switch or optionally an activation circuit 255 and the status of the AED 250 is provided by a visual indicator 256. The AED's circuit is provided on a PCB (not shown) contained within the housing 251, which also contains a low-cost, high-energy density battery (not shown) and pulse capacitor (not shown).

Figure 17:
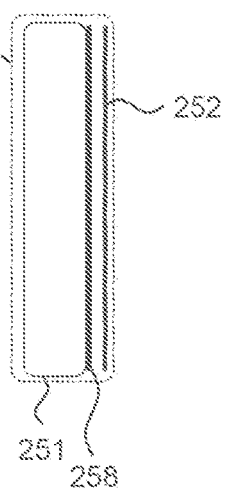
FIG. 17 is a side view showing the disposable single use pocketable AED of FIG. 10 with the housing and single free-floating electrode stowed in a carrying case.

FIG. 17 is a side view showing the disposable single use pocketable AED 250 of FIG. 10 with the housing 251 and single free-floating electrode 252 stowed in a carrying case. The single free-floating electrode 252 shares a similar profile with the housing 251.

Figure 18:
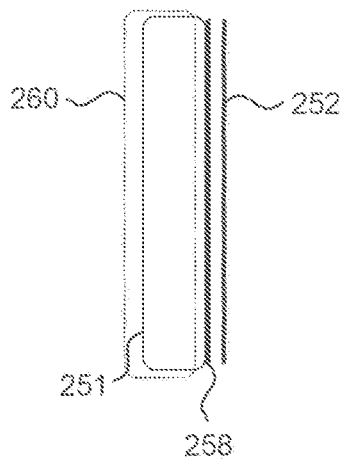
FIG. 18 is a side view showing the disposable single use pocketable AED of FIG. 10 with the housing and single free-floating electrodes partially deployed from the carrying case.

FIG. 18 is a side view showing the disposable single use pocketable AED of FIG. 10 with the housing and single free-floating electrodes partially deployed from the carrying case. The housing 251 and electrode 252 slide out of the carrying case 260 when being deployed. A smart cable management system (not shown) is also used to store the single lead 253 inside of the housing 251, where the lead is internally retracted by a cable management system until needed. The cable management system is further described below in detail with respect to FIGS. 25 and 26.

Figure 19:
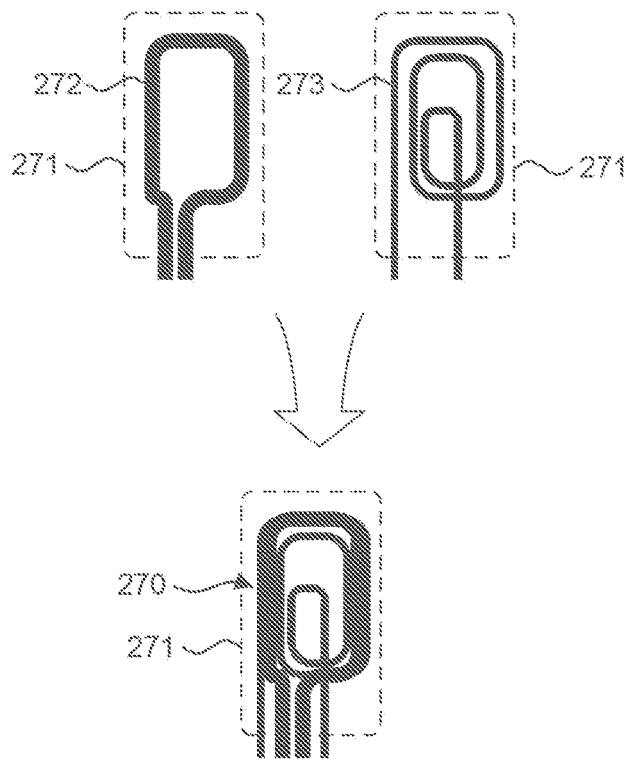
FIG. 19 is a top view diagram showing an electrode pad assembly for use in the disposable single use pocketable AEDs of FIGS. 10 and 15.

FIG. 19 is a top view diagram showing an electrode pad assembly 271 for use in the disposable single use pocketable AEDs 230, 250 of FIGS. 10 and 15. Each electrode contains an embedded planar laminated high energy pulse transformer. This type of transformer exhibits high power density by functioning at high switching frequencies, while packaged in a low profile with larger surface area, thereby preventing overheating. In each electrode assembly 271, a primary winding 272 and a secondary winding 273 are laminated together into a planar transformer 270 with a jumper that is soldered, welded, crimped, or otherwise electrically conducted together.

Figure 20:
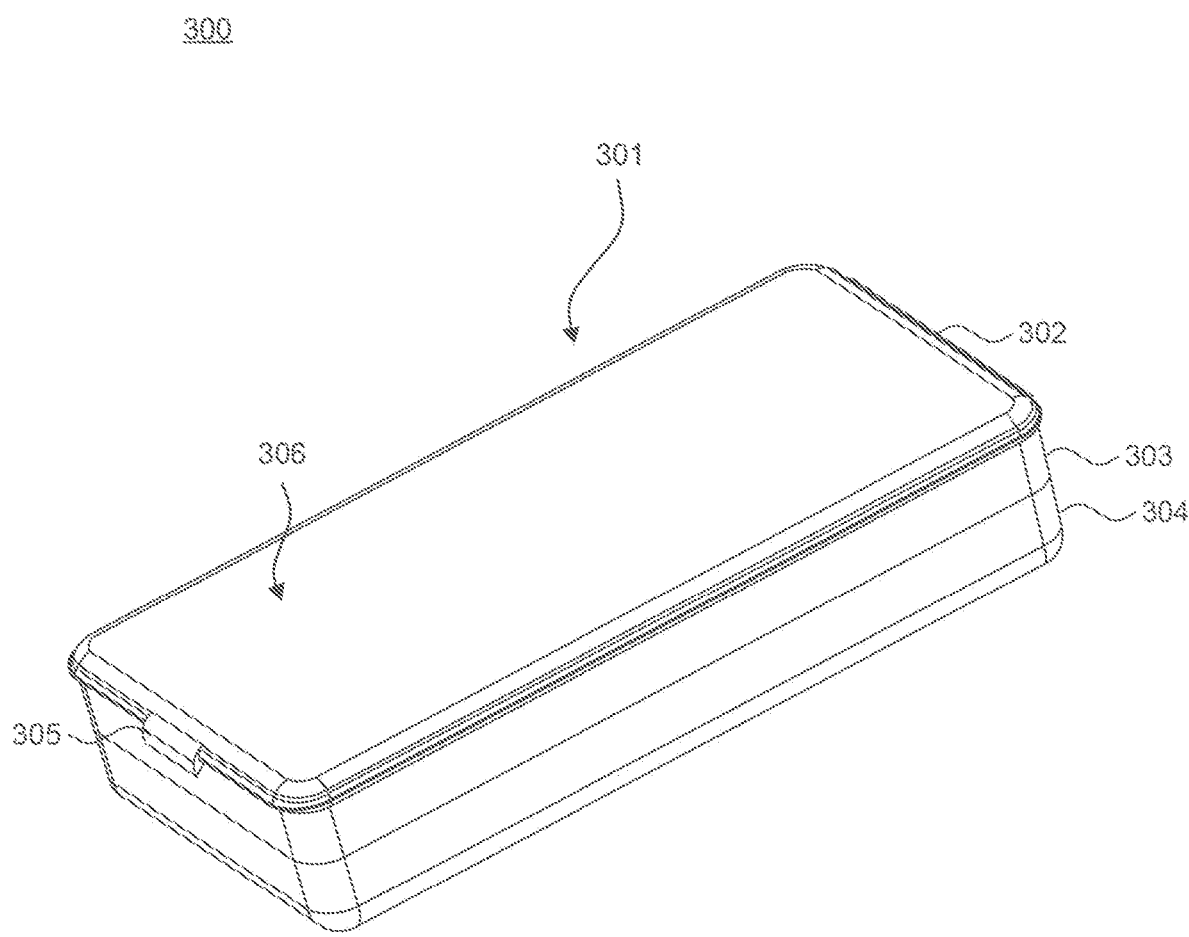
FIG. 20 is a perspective view diagram showing a case for a disposable, single use, pocketable AED.

To ensure the AED is small and light enough to easily carry, in a pocket, the case must also be small and light weight, as well as easy to use. Pads must be able to be effortlessly removed from the casing. Moreover, the case may be designed to trigger charging either upon removal or upon application of the electrode pads that automatically initiates condition or event detection and defibrillation. FIG. 20 is a perspective view 300 diagram showing a case 301 for a disposable, single use, pocketable AED. The case 301 can include a circuit enclosure 304, an electrode enclosure 303, and a cover 302. Each of the circuit enclosure 304, electrode enclosure 303, and cover 302 can have a rectangular shape and be made from metal, rigid plastic, flexible plastic, or another polymer. The case 301 can have a size in the range of 2.25 to 3.625 inches wide, 5.25 to 7 inches tall, and 0.25 to 1.875 inches deep and a weight in the range of 130 to 945 grams. Other shapes, sizes, and materials are possible.

The circuit enclosure 304 can house the energy storage circuit for generating defibrillation waveforms energy. In one embodiment, the circuit can be housed in a receptacle, which can be made from the same or different materials than the case, and affixed to a bottom surface of the electrode enclosure facing the circuit enclosure or a bottom surface of the circuit enclosure. The circuit is further described above with respect to FIGS. 3-7. The electrode enclosure 303 can house the electrode pads for placement on a patient and delivery of the defibrillation waveforms energy. The electrode enclosure can be stacked above the circuit enclosure 304 and can be fused to the circuit enclosure 304 using laser, ultrasonic, or radio frequency welding. Other methods for fusion are possible, such as joining the electrode enclosure and the circuit enclosure via fasteners.

In one example, the circuit enclosure 304 can include a bottom surface with four walls perpendicularly affixed around a perimeter of the bottom surface to form a cavity in which the energy storage circuit is housed, while the electrode enclosure 303 can also include a bottom surface with four walls perpendicularly affixed around a perimeter of the bottom surface to form a cavity in which the electrode pads are stored. The electrode enclosure 303 can be stacked on top of the circuit enclosure 304, and the bottom surface of the electrode enclosure 303 can be fused to a top surface of the circuit enclosure 304 walls, opposite the bottom surface of the circuit enclosure 304, to ensure the circuit enclosure and electrode enclosure are connected. When stacked, fused, fastened, or welded, access to the circuit enclosure is not possible, while still allowing access to the cavity of the electrode enclosure. The circuit enclosure 304 and the electrode enclosure 303 can have the same or different sizes. When different sizes, the circuit enclosure 304 can have a deeper cavity than the electrode enclosure, for example.

In a further embodiment, the electrode enclosure and the circuit enclosure can be stacked and snapped together to prevent separation. In one example, feet can be formed on a bottom surface of the electrode enclosure, such as one in each corner formed by the four walls. The circuit enclosure can include openings for the feet in each of the four corners formed by the walls of the circuit enclosure. When stacked, the feet are snapped into the openings to secure the electrode and circuit enclosures.

The cover 302 can be shaped and sized to fit over the cavity of the electrode enclosure 303 in which the electrode pads are housed and can allow or prevent access to the cavity depending on a position of the cover 302. In one embodiment, the cover 302 can be affixed to one or more walls of the electrode enclosure 303 and can include a fastener 305 on at least one side to keep the cover in a closed position for securing the electrode pads in the cavity of the electrode enclosure. The fastener 305 can include a latch, snap, or button, as well as other types of fasteners, and can be affixed to the cover on a side opposite the side affixed to the electrode enclosure 303. At a minimum, the fastener must prevent opening of the cover 302 when in a "closed" or "locked" position. Upon manual pressure, the fastener 305 is released to allow the cover to open and provide access to an interior of the electrode enclosure.

In a further embodiment, a single- or multi-step manual maneuver of any of the above fasteners can be utilized to ensure that accidental opening of the pads compartment does not occur. For example, a snap and a latch can be used to prevent accidental opening and ensure that the opening is intentional.

Figure 21:
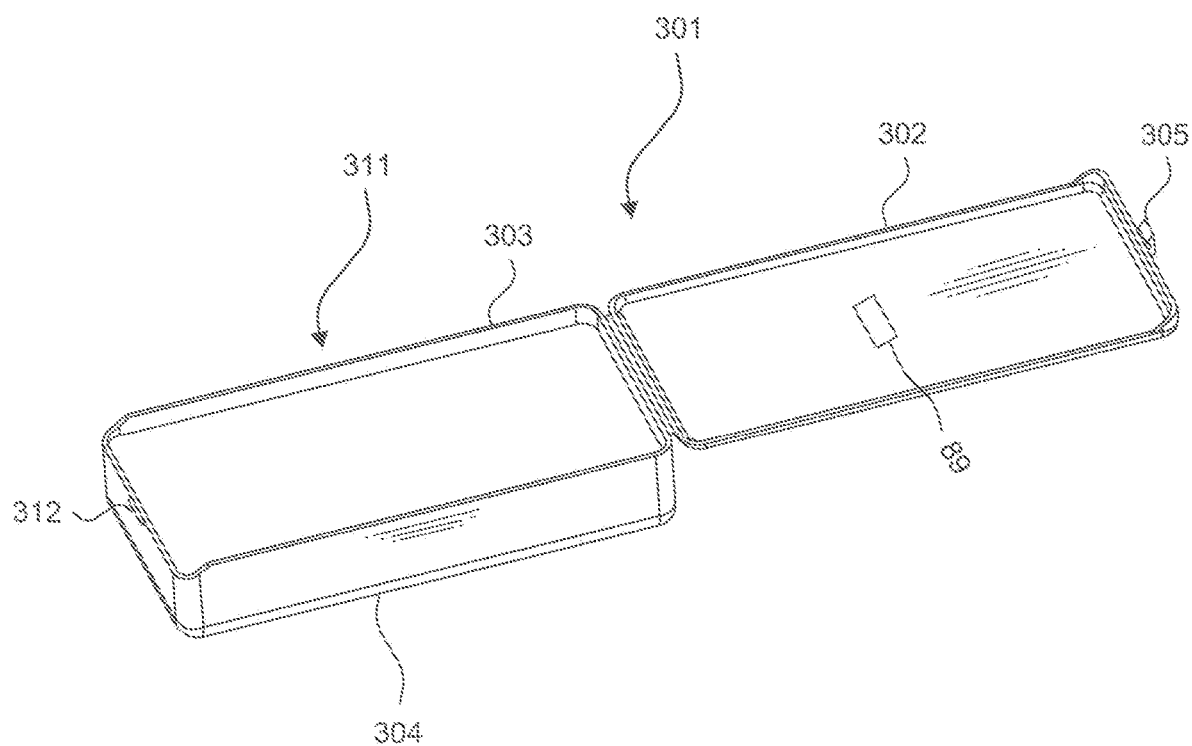
FIG. 21 is a perspective view diagram showing the case of FIG. 20 in an open position.

As described above, a magnet or user interfacing element (such as a button or a lever) included as part of a de-energizing component 89 can be placed on or in contact with the cover 302 to power up the device and commence charging of the energy storage circuit for delivery of energy to the pads when the AED is to be used on a patient, as shown with reference to FIG. 21. Specifically, when the fastener 305 is unlocked, the pads are removed, or the cover 302 is opened, the de-energizing component 89 is actuated and charging of the energy storage circuit is initiated. If, for some reason, the cover is unintentionally opened despite the safety precautions of the fasteners, the automatic charging can terminate upon closing of the case, as described above with reference to FIG. 8

To improve the usability of the AED by inexperienced, confused, or frightened lay users, a top surface of the cover 302 can include a user interface 306 that does not require a screen or buttons. This approach reduces confusion amongst various population groups such as low English literacy or the elderly, as well as those confused over what happens during SCA. The significant upside to this approach is that the simpler the interface, the quicker a shock is delivered and the likelihood of survival increases. The user interface 306 can include simple instructional wording and artwork for utilizing the AED, such as "Open" with an arrow pointing to the location of opening. In one embodiment, the instructions can be provided on the relevant parts of the case by printing the instructions on the case, generating labels or stickers with the instructions for sticking on the case, or by embossing the instructions on the case. Such instructions, which can include one or more words, can be placed on the case itself, pouch, or electrode pads.

Further, the user interface 306 can include lights that signal various instructions and/or alerts to the user. The user interface 306 can also be included on an interior surface of the cover 302, as well as on a back surface of the case 301. Other locations for the user interface are possible. Surfaces 353 or the inside of 303 can also serve as the user interface. In addition to the visual interface, a tonal warning can sound prior to the delivery of shock. The elimination of verbal instructions further reduces confusion amongst various populations such as low English literacy or the elderly. However, in a further embodiment, the user interface can include a display screen or manual buttons (not shown).

When the AED is needed, the cover can be opened to access the electrode pads. FIG. 21 is a perspective view 310 diagram showing the case 301 of FIG. 20 in an open position. The cover 302 is attached on one end to a wall of the electrode enclosure 303. The cover 302 can be attached, on one side, via a hinge, living hinge, screw, bracket, or other mechanism that will allow the cover to rotate to open and closed positions to allow and prevent access to the electrode enclosure cavity, respectively. Rotation of the cover can occur on any side of the cover to allow opening of the case lengthwise or widthwise. The cover 302 can also be attached to the wall of the electrode enclosure 303 via a hinge. When the cover 302 is rotated in an open position, access to a cavity 311 of the electrode enclosure is available. A fastening device 305, such as a clasp or latch can be affixed to an end of the cover opposite the end affixed to the electrode enclosure to prevent unintended opening of the cover 302. In one embodiment, the fastening device can include a V-shape or check mark shaped mechanism to fasten over a stopper 312 affixed to an outer surface of the electrode enclosure wall opposite the wall to which the cover is affixed. As described above, the de-energizing component 89 can be positioned on (or embedded in) the cover 302 of the case and removal or movement of the cover 302 causes the energizing of the AED. In a different configuration of the case 301, the de-energizing component 89 could be positioned on (or embedded in) other removable or movable portions of the case, such as a PCBA enclosure or electrode enclosure, though other components of the case to which the de-energizing component 89 could be linked are also possible. Movement or removal of such components of the case causes the energizing of the AED. For example, one way to energize the AED is removal or movement of the cover 302 of the enclosure.

Figure 22:
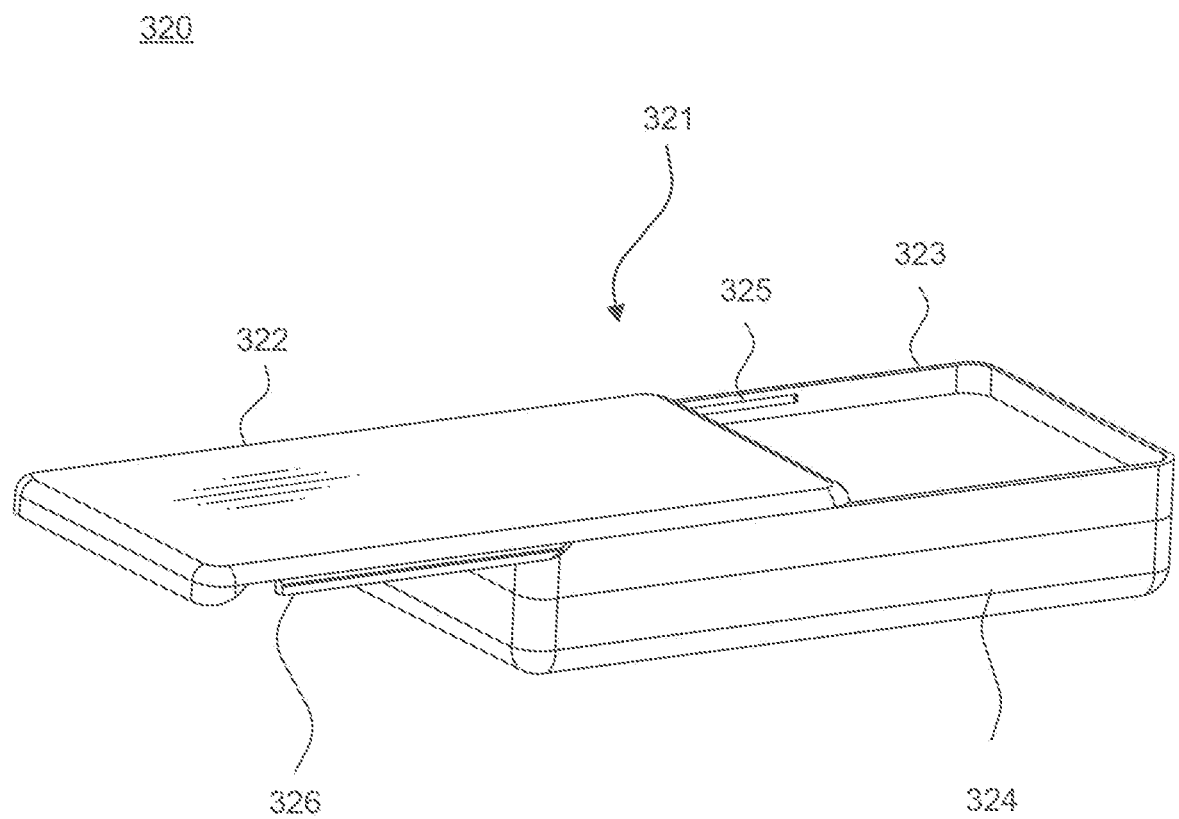
FIG. 22 is a perspective view diagram showing a case for the disposable single use pocketable AED with an alternative opening mechanism.

The cover can also be attached using rails or slides. FIG. 22 is a perspective view 320 diagram showing a case 321 for the disposable single use pocketable AED with an alternative opening mechanism. The case 321 includes a cover 322, an electrode enclosure 323, and a circuit enclosure 324. The cover can control access to an interior of the case, specifically, a cavity of the electrode enclosure, by sliding open and closed.

A pair of slides 326 can be affixed on a bottom surface of the cover, which faces the cavity of the electrode enclosure. Each slide 326 can be affixed on opposite sides of the cover along a length of the case. Tracks 325 are affixed to an interior of the electrode enclosure along opposite walls. The slides 326 of the cover 322 can move back and forth along the tracks 325 to move the cover 322 to open and closed positions. Movement of the cover can occur manually with a user sliding the cover along the tracks. A locking mechanism (not shown) can be included, such as a fastener or hook to prevent unintentional movement of the cover. Additionally, the two-step manual maneuver and process to prevent unintentional opening can also be utilized.

Figure 23:
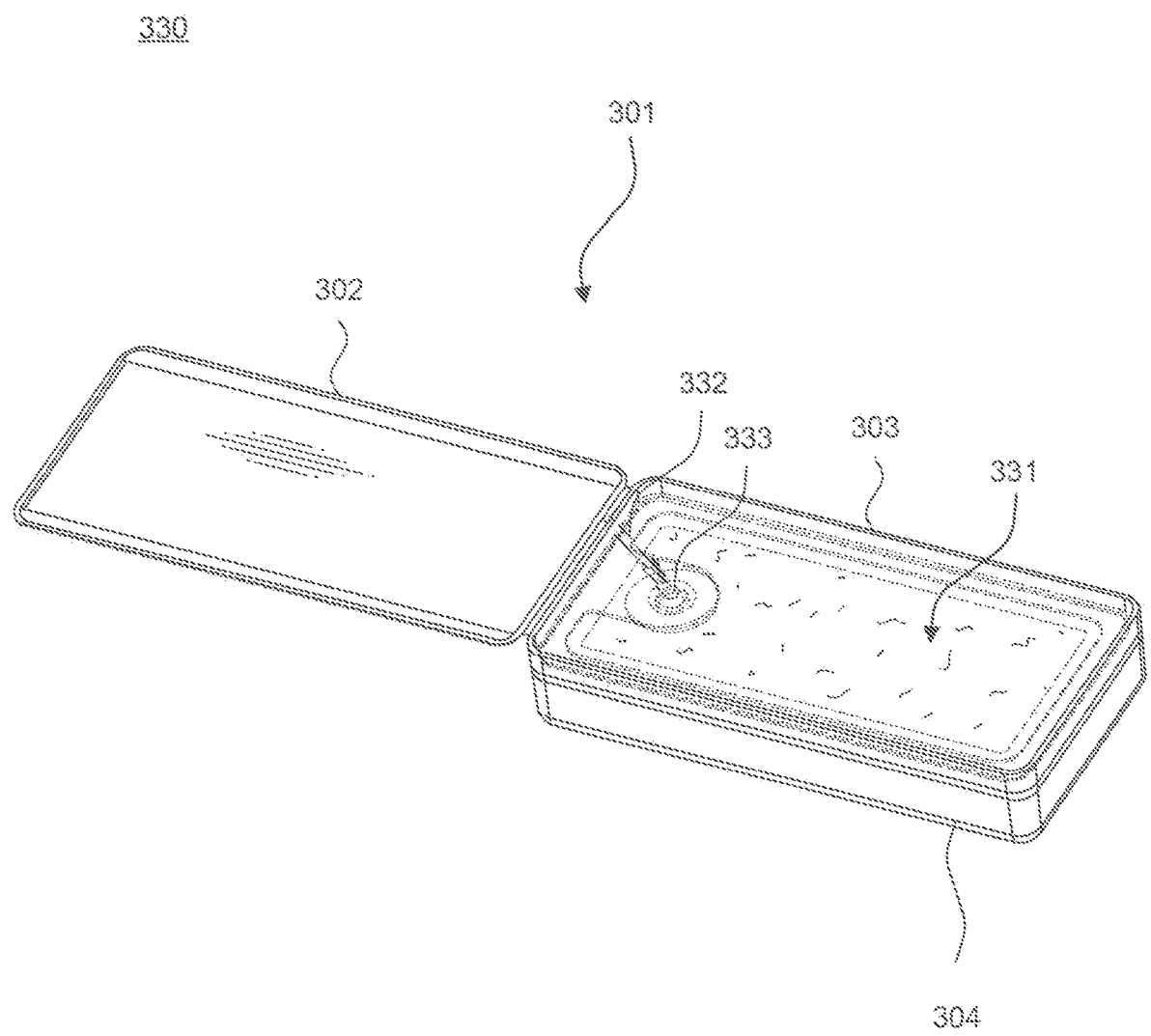
FIG. 23 is a perspective view diagram showing the case of FIG. 20 in an open position with electrode pads.

The cavity or interior of the electrode enclosure can be shaped and sized to house the electrode pads, which can lay flat or folded in some manner in the electrode enclosure. FIG. 23 is a perspective view 330 diagram showing the case 301 of FIG. 20 in an open position with electrode pads 331. A pair of the electrode pads 331 can lay directly on a bottom surface of the electrode enclosure with one electrode pad stacked on top of another electrode pad. In a further embodiment, the electrode pads can lay on a boss provided in the electrode enclosure, as described in detail below with reference to FIG. 25.

In the embodiment that the pads are placed directly inside the cavity of the electrode enclosure 303, then the Moisture Vapor Transmission Rate (MVTR) of the electrode enclosure can be improved by use of coatings, lamination, or vapor deposition of MVTR-reducing materials. A decreased MVTR is beneficial as it increases the time the electrodes remain at the ideal hydration range. An increased duration of storage at the ideal hydration range can equate to longer shelf life.

In another embodiment the pads are placed inside a hygienic pouch or container that is placed inside the cavity of the electrode enclosure 303 to prevent contamination or damage to the pads. The pouch can be poly foil or other type of hygienic material. To reduce size of the overall AED, the wires inside the pouch may be managed with various cable management techniques, such as disposable wraps. An electrode pouch often has excess size beyond the size of the electrode it contains. This excess area often includes air gaps around the electrode to prevent heat sealing from damaging the electrodes, as well as includes the heat seal locations. To additionally reduce the size of the AED, the excess areas of the pouch can be folded to increase the compactness of the pad assembly that is placed inside the cavity. When needed, the electrode pads can be removed from the pouch by unsealing, tearing open, or unfolding the pouch.

The electrode pads 331 can each include a wire 332 affixed via a connector 333 on the pad. The wires 332 can extend from the electrode pads 331 and connect to the energy storage circuit (not shown) housed in the circuit enclosure 304. When placed in a pouch, the wires can extend from the pads outside the patch and to the circuit.

The wires can connect the electrode pads and circuit via a metal or plastic feedthrough mechanism, such as a tube, through the electrode enclosure. In a further embodiment, the feedthrough mechanism can be formed in a bottom surface of the electrode enclosure as a hole in the shape of a circle, rectangle, square, or other shape to allow the wires in the electrode enclosure to access the circuit in the circuit enclosure. In one embodiment, the wires can be hardwired to the circuit to prevent displacement of the wires from the circuit. A strain relief can also be used with the feedthrough to prevent pulling of the wires from the circuit. For example, the wires can be glued in or to the feedthrough.

The wires can be longer than a length of the case and must be wrapped or folded to fit to reach the victim's chest from the AEDs position to the side of their chest. In one example, the wires are at least 3 ft. long and can be wrapped around an interior of the electrode enclosure, in the cavity. In a further example, the wires can lay on top of the top electrode pad, and in yet a further example, the wires can be wrapped around a boss as further described in detail below with respect to FIG. 25.

Each electrode pad can include an adhesive on at least a portion of one side to affix to a chest of a patient. The adhesive is protected by a liner (not shown) that can be removed prior to placement of the pad on the patient.

Figure 24:
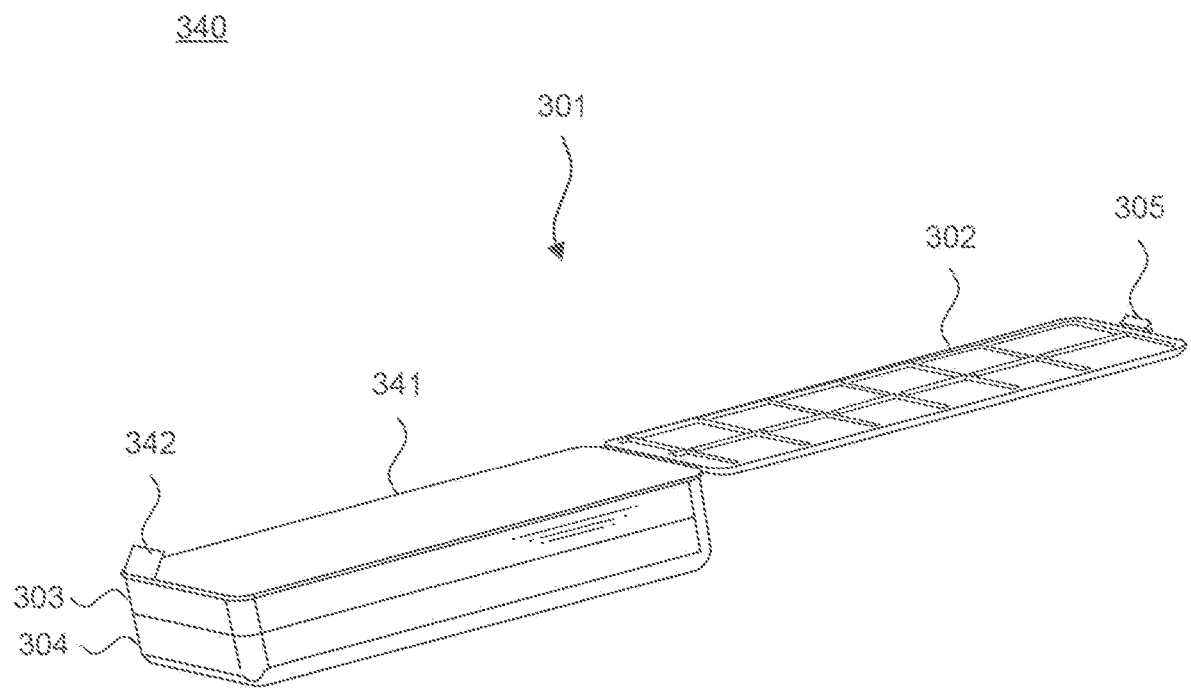
FIG. 24 is a perspective view diagram showing the case of FIG. 20 in an open position with a seal.

When a pouch is not used, a seal can be used to protect the electrode pads and ensure the pads are hygienic and operable when needed. FIG. 24 is a perspective view 340 diagram showing the case 301 of FIG. 20 in an open position with a seal. The cover 302 of the case is in an open position, which can provide access to an interior of the case, including the electrode enclosure 303. A seal 341 is secured over the cavity of the electrode enclosure 303 and electrode pads (not shown). The seal can be made of a layer of nylon, foil, or polypropylene. However, other types of material for the seal are possible. At a minimum, the material should have a moisture vapor transmission rate equal or less than 0.0005 $g/in^{2/24}$. The seal 341 can be sized to fit over the electrode enclosure cavity and attach to a top surface of the walls of the electrode enclosure 303. The seal 341 can include a tab 342 on one side, or multiple sides, so that a user can pull the tab to remove the seal. When the electrode pads are placed in a pouch, the seal is not necessary, but can be used.

Figure 25:
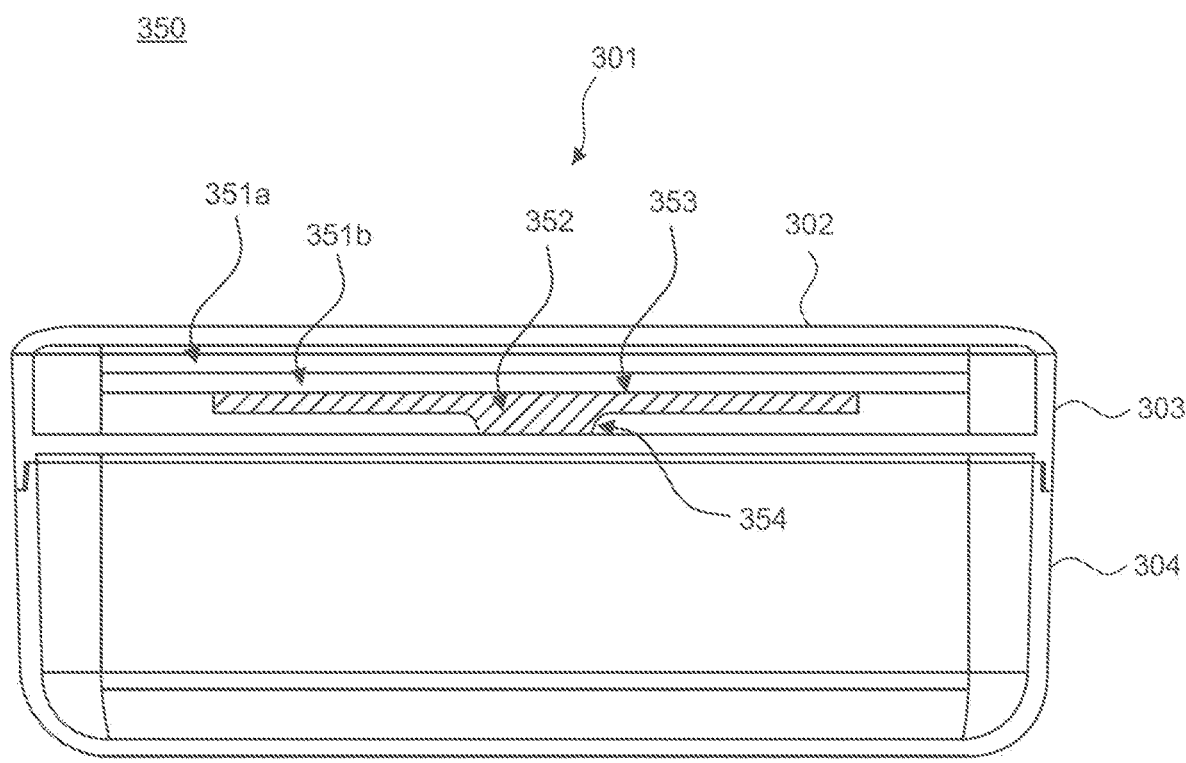
FIG. 25 is a side view cross section showing the case of FIG. 20 with a boss in the electrode enclosure.

A magnet or mechanical trigger can be affixed to the electrode pads, pouch in which the electrode pads are stored, or the seal to initiate charging of the electrical pads. For example, when the seal is removed from the electrode enclosure, the energy storage circuit can begin charging. In a further example, charging can be initiated when the pouch is opened, or the electrode pads are removed from the electrode enclosure. Whether the electrode pads are directly placed in the electrode enclosure or placed in a pouch, the electrode pads can lay on a bottom surface of the electrode enclosure or on a boss above the bottom surface of the electrode enclosure. FIG. 25 is a side view cross section 350 showing the case 301 of FIG. 20 with a boss 352 in the electrode enclosure. A boss 352 can be placed in the cavity of the electrode enclosure 303 of the case 301 to hold the electrode pads 351*a, b* and organize the wires (not shown), while simultaneously providing space for the circuit underneath. The pads can rest on top of the boss, above where the wires are wrapped, thus making more compact the form factor of the electrode enclosure. It will likewise provide more space for the energy storage circuit.

The boss 352 can be made of a single piece of material and comprise a three-dimensional shape, such as an oval or rectangle, as well as other shapes. Alternatively, the boss 352 can include a stand 354 affixed to a bottom surface of the electrode enclosure 303 and can be shaped as a circle, rectangle, square, or other shapes. A flat surface 353 that is the same size as or smaller than the electrode pads is affixed to the stand 354. The flat surface holds the electrode pads 351*a, b* above the bottom surface of the electrode enclosure 303, while the wires attached to the electrode pads wrap around the stand. Other configurations for storing the wires are possible. The electrode pads 351*a, b* can be stored on top of one another. When the pads are non-flat, the flat surface of the bottom surface of the electrode enclosure or the boss helps the non-flat pads to lay flat.

Figure 26:
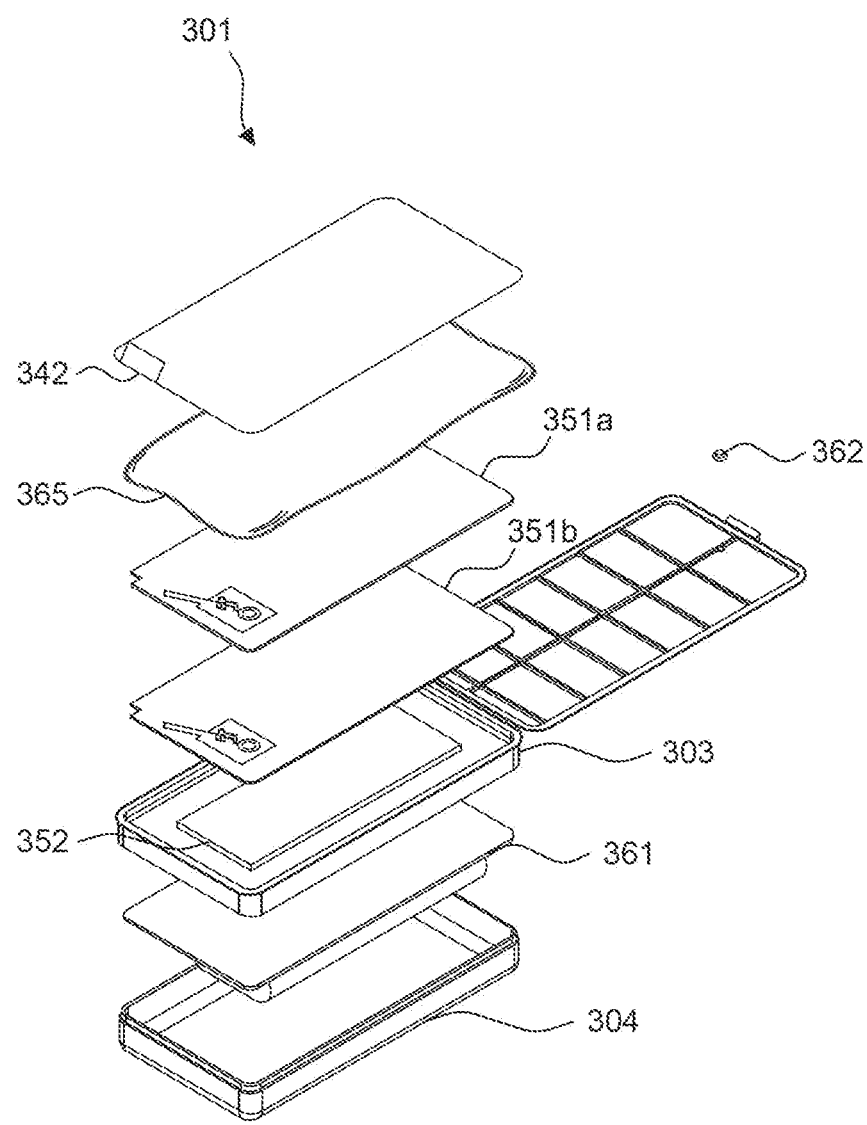
FIG. 26 is an exploded view showing the case of FIG. 20.

The AED case is specialized and specifically configured for secure storage of the AED circuit, as well as quick deployment of the AED, such as affixing the pads to the patient and initiating energy to the pads for delivery to the patient. FIG. 26 is an exploded view 360 showing the case 301 of FIG. 20. The bottom of the case includes the circuit enclosure 304 in which the energy storage circuit 361 for the AED is housed. The electrode enclosure 303 with boss 352 is located over or above the circuit enclosure 304. The electrode pads 351*a, b* are placed on a top surface of the boss 352 and a seal 341 with a tab 342 covers the electrode pads 351*a, b*. The boss provides more space for the energy storage circuit; however, the electrode pads 351*a, b* can also be placed directly in the electrode enclosure 303 without the boss 352. In one embodiment, the electrode pads 351 a, b can be placed in a pouch 365 prior to placement on the boss 352 or directly in the electrode enclosure 303. If necessary to fit within the case, the pouch 365 can be folded. A magnet or mechanical trigger 362 is placed on one or more of the cover 302, electrode pads 351*a, b*, pouch 365 in which the electrode pads 351*a, b* are stored, or electrode enclosure 303 to initiate charging of the AED upon trigger of the magnet or manual trigger.

Figure 27:
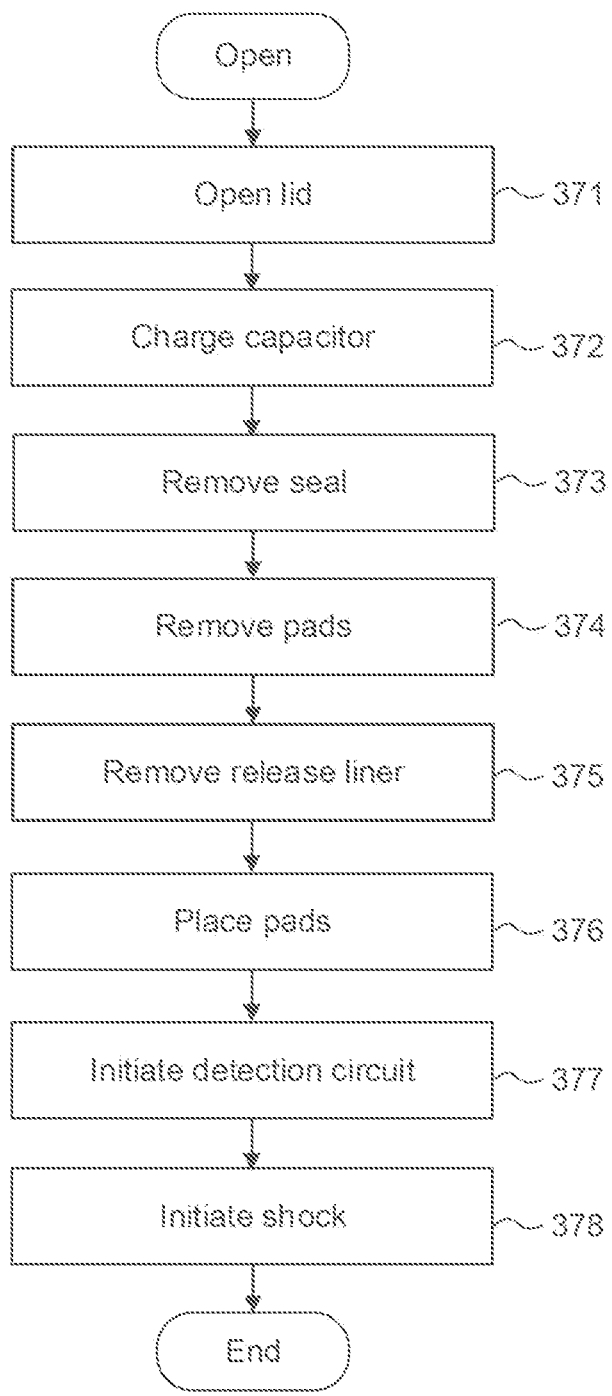
FIG. 27 is a flow diagram showing a process for using the AED housed in the case.

In addition to ensuring the case is easily accessible and always available, the case must also be easy to open and facilitate easy use of the AED. FIG. 27 is a flow diagram showing a process 370 for using the AED housed in the case. When a person is in need of defibrillation, the case can be pulled out of a pocket, purse, or carrying case of a user or from another location. The cover of the case is opened (step 371), such as by sliding the cover to an open position or releasing a fastener on the cover. Once opened, charging (step 372) of the capacitor can begin. A user can remove (step 373) the seal over the electrode enclosure or tear open a pouch contained inside of electrode enclosure 303 to access the electrode pads. The electrode pads are removed (step 374) from the case or pouch, and the user removes (step 375) the liners from the pads to stick (step 376) the pads to a patient's chest. Based upon a trigger or manual action, an activity detection circuit (step 377) is initiated to detect whether a shockable event of the patient, such as ventricular fibrillation, is detected. The trigger can include application of the pads to the patient's chest or removal of the pads from the case, while a manual action can include a button press to initiate charging and detection analysis for a shockable event. The charging and activity detection can occur simultaneously or sequentially. When performed sequentially, charging of the capacitor can begin upon pad application to the patient and before the detection algorithm is satisfied.

If a shockable event is detected, one or more shocks are provided (step 378) to the patient. In one embodiment, up to six shocks can be administered to the patient. When multiple shocks are necessary, activity detection can be applied after each shock to determine whether an additional shock is needed.

While components of the AED, such as the case and pads can be single use and disposable, the circuit can be reusable. For example, after the AED has been used, the circuit can be removed from the used case and placed into a new case with new pads and wires. However, in a further embodiment, the AED case can also be reusable. After use, the circuit and pads can be removed. The pads can be disposed of, while the circuit can be cleaned and replaced in the case with new pads.

Regardless of whether the case is to be reused, the case must be opened to access the circuit for reuse. Opening of the case is dependent on how the electrode enclosure and the circuit enclosure were joined. For example, if the two enclosures were welded together, laser cutting can be used to separate the two enclosures. Alternatively, if the two enclosures are screwed together, a torque controlled screwdriver can be used to separate the enclosures. Once opened, the battery can be removed from the circuit board, the circuit board can be washed and cleaned, and a new battery can be placed on the circuit board for use in another housing or case, along with new pads. The circuit board can only be reused once the patient data and logs from the previous use are offloaded.

The circuit described herein provides for the delivery of a high-voltage, high energy pulse for use in external defibrillation through a design that decreases overall device cost, size, and weight by meaningfully innovating alternatives to capacitor charging through the use of low voltage, high current supplementary defibrillation energy storage and delivery. The circuit enables high energy densities with low cost, weight, and size.

In addition, the circuit provides the basis for external defibrillators that are easy to carry, low cost and lightweight, while delivering a high-voltage, high-energy biphasic shock suitable for cardiac defibrillation and victim resuscitation. External defibrillators utilizing this circuit can help to facilitate the widespread adoption of the portable defibrillation technology and thereby meaningfully help to decrease the number of deaths from sudden cardiac arrest. Moreover, such circuits could also aid in reducing size and cost of implantable defibrillators. Additionally, the casing design adds to size reduction, simplicity and cost reduction of the AED.

While the invention has been particularly shown and described as referenced to the embodiments thereof, those skilled in the art will understand that the foregoing and other changes in form and detail may be made therein without departing from the spirit and scope of the invention.

What is claimed is:

1. A de-energizable defibrillation assembly, comprising:
   an electromechanical component;
   an energy storage element that supplies power to the electromechanical component; and
   circuitry configured to generate a defibrillation waveform, the circuitry comprising a microcontroller control, element configured to run a diagnostic check upon the circuitry receiving the power from the energy storage element, wherein the circuitry is isolated from the energy storage element by the electromechanical component and wherein the circuitry is electrically unbiased when the power is not flowing from the energy storage element to the circuitry through the electromechanical component.

2. A de-energizable defibrillation assembly in accordance to claim 1, wherein the electromechanical component comprises a switch that is in an open position when the circuitry is not in use.

3. A de-energizable defibrillation assembly in accordance to claim 2, wherein the switch comprises a magnetically triggered reed switch.

4. A de-energizable defibrillation assembly in accordance to claim 2, wherein the switch comprises a mechanical switch.

5. A de-energizable defibrillation assembly in accordance to claim 1, further comprising:
   one or more mobile components, wherein a removal of one or more of the mobile components from an initial position to a further position affects the electromechanical component to cause the power to flow to the circuitry through the electro-mechanical component.

6. A de-energizable defibrillation assembly in accordance to claim 5, wherein one or more of the removable components comprise packaging provided to enclose at least a portion of one or more of electrode pads through which the defibrillation waveform is delivered to a patient.

7. A de-energizable defibrillation assembly in accordance to claim 6, wherein the packaging comprises a pouch within which the electrode pads are stored.

8. A de-energizable defibrillation assembly in accordance to claim 6, wherein the packaging comprises a seal.

9. A defibrillation assembly energizable through packaging removal, comprising:
   an electromechanical component;
   an energy storage element that supplies power to the electromechanical component;
   circuitry configured to generate a defibrillation waveform, the circuitry comprising a microcontroller control element, wherein the circuitry is isolated from the energy storage element by the electromechanical component and wherein the circuitry is electrically unbiased when the power is not flowing from the energy storage element to the circuitry through the electromechanical component; and
   one or more mobile components, wherein a removal of one or more of the mobile components from an initial position to a further position affects the electromechanical component to cause the power to flow to the circuitry through the electromechanical component and wherein one or more of the removable components comprise packaging provided to enclose at least a portion of one or more of electrode pads through which the defibrillation waveform is delivered to a patient.

10. A de-energizable defibrillation assembly, comprising:
    a defibrillator, comprising:
    an electromechanical component;
    an energy storage element that supplies power to an entirety of circuitry of the defibrillator via the electromechanical component;
    the entirety of the circuitry comprising a microcontroller control element and configured to generate a defibrillation waveform, wherein the entirety of the circuitry is isolated from the energy storage element by the electromechanical component and wherein the entirety of the circuitry is electrically unbiased when the power is not flowing from the energy storage element to the entirety of the circuitry through the electromechanical component.

* * * * *